US011833206B2

(12) United States Patent
Yadav et al.

(10) Patent No.: US 11,833,206 B2
(45) Date of Patent: Dec. 5, 2023

(54) POLYSORBATE MIXTURES HAVING MODIFIED FATTY ACID ESTER DISTRIBUTION

(71) Applicant: Genentech, Inc., South San Francisco, CA (US)

(72) Inventors: Sandeep Yadav, South San Francisco, CA (US); Nidhi Doshi, South San Francisco, CA (US); Tamanna Shobha, South San Francisco, CA (US); Anthony Tomlinson, South San Francisco, CA (US); Amit Srivastava, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 71 days.

(21) Appl. No.: 17/483,234

(22) Filed: Sep. 23, 2021

(65) Prior Publication Data

US 2022/0111054 A1 Apr. 14, 2022

Related U.S. Application Data

(60) Provisional application No. 63/168,567, filed on Mar. 31, 2021, provisional application No. 63/082,606, filed on Sep. 24, 2020, provisional application No. 63/082,611, filed on Sep. 24, 2020.

(51) Int. Cl.
*A61K 47/26* (2006.01)

(52) U.S. Cl.
CPC ................... *A61K 47/26* (2013.01)

(58) Field of Classification Search
CPC ...................................................... A61K 47/26
See application file for complete search history.

(56) References Cited

PUBLICATIONS

Mridula Dwivedi, Michaela Blech, Ingo Presser, Patrick Garidel, Polysorbate degradation in biotherapeutic formulations: Identification and discussion of current root causes, International Journal of Pharmaceutics, vol. 552, Issues 1-2, 2018.*
United States Pharmacopeia, Polysorbate 20, Interim Revision Announcement Official Sep. 1, 2014.*
Ariadna Martos, Wendelin Koch, Wim Jiskoot, Klaus Wuchner, Gerhard Winter, Wolfgang Friess, Andrea Hawe, Trends on Analytical Characterization of Polysorbates and Their Degradation Products in Biopharmaceutical Formulations, Journal of Pharmaceutical Sciences, vol. 106, Issue 7,2017.*
Doshi Nidhi et al., "Evaluating a Modified High Purity Polysorbate 20 Designed to Reduce the Risk of Free Fatty Acid Particle Formation", Pharmaceutical Research, vol. 38, No. 9, Sep. 1, 2021, pp. 1563-1583.
Doshi Nidhi et al., "Evaluating of Super Refined Polysorbate 20 With Respect to Polysorbate Degradation, Particle Formation and Protein Stability", Journal of Pharmaceutical Sciences, vol. 109, No. 10, Oct. 1, 2020, pp. 2986-2995.
Doshi Nidhi et al., "Understanding Particle Formation: Solubility of Free Fatty Acids as Polysorbate 20 Degradation Byproducts in Therapeutic Monoclonal Antibody Formulations", Molecular Pharmaceutics, ACS Publications, vol. 12, No. 11, Nov. 2, 2015, pp. 3792-3804.
Dwivedi Mridula et al., "Polysorbate degradation in biotherapeutic formulations: Identification and discussion of current root causes", International Journal of Pharmaceutics, vol. 552, No. 1, Oct. 6, 2018, pp. 422-436.
PCT International Search Report from PCT/US2021/051681, dated Mar. 4, 2022, 3 pages.
Written Opinion of the International Searching Authority from PCT/US2021/051681, dated Mar. 4, 2022, 7 pages.
Allmendinger A, Lebouc V, Bonati L, Woehr A, Kishore RS, Abstiens K. Glass leachables as a nucleation factor for free fatty acid particle formation in biopharmaceutical formulations. Journal of Pharmaceutical Sciences. 2021;110(2):785-95.
Bam NB, Cleland JL, Yang J, Manning MC, Carpenter JF, Kelley RF, et al. Tween protects recombinant human growth hormone against agitation-induced damage via hydrophobic interactions. J Pharm Sci. 1998;87(12):1554-9.
Benito-Gallo P, Franceschetto A, Wong JC, Marlow M, Zann V, Scholes P, et al. Chain length affects pancreatic lipase activity and the extent and pH-time profile of triglyceride lipolysis. European journal of pharmaceutics and biopharmaceutics. 2015;93:353-62.
Chiu J, Valente KN, Levy NE, Min L, Lenhoff AM, Lee KH. Knockout of a difficult-to-remove CHO host cell protein, lipoprotein lipase, for improved polysorbate stability in monoclonal antibody formulations. Biotechnol Bioeng. 2017;114(5):1006-15.
Dixit N, Salamat-Miller N, Salinas PA, Taylor KD, Basu SK. Residual Host Cell Protein Promotes Polysorbate 20 Degradation in a Sulfatase Drug Product Leading to Free Fatty Acid Particles. J Pharm Sci. 2016;105(5):1657-66.
Doshi N, Demeule B, Yadav S. Understanding Particle Formation: Solubility of Free Fatty Acids as Polysorbate 20 Degradation Byproducts in Therapeutic Monoclonal Antibody Formulations. Mol Pharm. 2015;12(11):3792-804.
Doshi N, Fish R, Padilla K, Yadav S. Evaluation of Super RefinedTM Polysorbate 20 With Respect to Polysorbate Degradation, Particle Formation and Protein Stability. Journal of Pharmaceutical Sciences. 2020;109(10):2986-95.
Doshi N, Giddings J, Luis L, Wu A, Ritchie K, Liu W, Chan W, Taing R, Chu J, Sreedhara A, Kannan A. A Comprehensive Assessment of All-Oleate Polysorbate 80: Free Fatty Acid Particle Formation, Interfacial Protection and Oxidative Degradation. Pharmaceutical Research. 2021:1-8.
Doshi N, Martin J, Tomlinson A. Improving Prediction of Free Fatty Acid Particle Formation in Biopharmaceutical Drug Products: Incorporating Ester Distribution during Polysorbate 20 Degradation. Mol Pharm. 2020. ;17(11):4354-63.

(Continued)

*Primary Examiner* — Jeffrey S Lundgren
*Assistant Examiner* — Eric Tran
(74) *Attorney, Agent, or Firm* — McNeill Baur PLLC

(57) ABSTRACT

The present disclosure provides polysorbate 20 compositions with particular fatty acid ester concentrations. In some embodiments, they may be used in pharmaceutical formulations, for example, to improve stability.

29 Claims, 13 Drawing Sheets

(56) References Cited

PUBLICATIONS

Dwivedi M, Blech M, Presser I, Garidel P. Polysorbate degradation in biotherapeutic formulations: identification and discussion of current root causes. International journal of pharmaceutics. 2018;552(1-2):422-36.

Fish R, Lin J, Doshi N. Impact of Silicone Oil on Free Fatty Acid Particle Formation due to Polysorbate 20 Degradation. Pharmaceutical Research. 2020;37(11):1-15.

Gopalrathnam G, Sharma AN, Dodd SW, Huang L. Impact of stainless steel exposure on the oxidation of polysorbate 80 in histidine placebo and active monoclonal antibody formulation. PDA journal of pharmaceutical science and technology. 2018;72(2):163-75.

Ha E, Wang W, Wang YJ. Peroxide formation in polysorbate 80 and protein stability. J Pharm Sci. 2002;91(10):2252-64.

Hall T, Sandefur SL, Frye CC, Tuley TL, Huang L. Polysorbates 20 and 80 degradation by group XV lysosomal phospholipase A2 isomer X1 in monoclonal antibody formulations. Journal of pharmaceutical sciences. 2016;105(5):1633-42.

Kerwin BA. Polysorbates 20 and 80 used in the formulation of protein biotherapeutics: structure and degradation pathways. J Pharm Sci. 2008;97(8):2924-35.

Kranz W, Wuchner K, Corradini E, Berger M, Hawe A. Factors Influencing Polysorbate's Sensitivity Against Enzymatic Hydrolysis and Oxidative Degradation. J Pharm Sci. 2019;108(6):2022-32.

Labrenz SR. Ester hydrolysis of polysorbate 80 in mAb drug product: evidence in support of the hypothesized risk after the observation of visible particulate in mAb formulations. J Pharm Sci. 2014;103(8):2268-77.

Lapelosa M, Patapoff TW, Zarraga IE. Molecular simulations of micellar aggregation of polysorbate 20 ester fractions and their interaction with N-phenyl-1-naphthylamine dye. Biophys Chem. 2016;213:17-24.

Li Y, Hewitt D, Lentz YK, Ji JA, Zhang TY, Zhang K. Characterization and stability study of polysorbate 20 in therapeutic monoclonal antibody formulation by multidimensional ultrahigh-performance liquid chromatography-charged aerosol detection-mass spectrometry. Analytical chemistry. 2014;86(10):5150-7.

Mahler H-C, Huber F, Kishore RS, Reindl J, Rückert P, Müller R. Adsorption behavior of a surfactant and a monoclonal antibody to sterilizing-grade filters. Journal of pharmaceutical sciences. 2010;99(6):2620-7.

Mahler HC, Printz M, Kopf R, Schuller R, Muller R. Behaviour of polysorbate 20 during dialysis, concentration and filtration using membrane separation techniques. J Pharm Sci. 2008;97(2):764-74.

McShan AC, Kei P, Ji JA, Kim DC, Wang YJ. Hydrolysis of Polysorbate 20 and 80 by a Range of Carboxylester Hydrolases. PDA J Pharm Sci Technol. 2016;70(4):332-45.

Nayem J, Zhang Z, Tomlinson A, Zarraga IE, Wagner NJ, Liu Y. Micellar morphology of Polysorbate 20 and 80 and their ester fractions in solution via Small Angle Neutron Scattering. Journal of Pharmaceutical Sciences. 2019.

Saggu M, Demeule B, Jiang L, Kammerer D, Nayak PK, Tai M, Xiao N, Tomlinson A. Extended Characterization and Impact of Visible Fatty Acid Particles—A Case Study With a mAb Product. Journal of Pharmaceutical Sciences. 2021;110(3):1093-102.

Saggu M, Liu J, Patel A. Identification of Subvisible Particles in Biopharmaceutical Formulations Using Raman Spectroscopy Provides Insight into Polysorbate 20 Degradation Pathway. Pharm Res. 2015;32(9):2877-88.

Shinomiya M, McLean L, Jackson RL. Chain length dependence of phosphatidylcholine hydrolysis catalyzed by lipoprotein lipase. Effect of apolipoprotein C-II. Journal of Biological Chemistry. 1983;258(23):14178-80.

Siska CC, Pierini CJ, Lau HR, Latypov RF, Fesinmeyer RM, Litowski JR. Free fatty acid particles in protein formulations, part 2: contribution of polysorbate raw material. J Pharm Sci. 2015;104(2):447-56.

Tomlinson A, Demeule BI, Lin B, Yadav S. Polysorbate 20 degradation in biopharmaceutical formulations: quantification of free fatty acids, characterization of particulates, and insights into the degradation mechanism. Molecular pharmaceutics. 2015;12(11):3805-15.

Tomlinson A, Zarraga IE, Demeule B. Characterization of Polysorbate Ester Fractions and Implications on Protein Drug Product Stability. Molecular Pharmaceutics. 2020.

Zhang L, Yadav S, Demeule B, Wang YJ, Mozziconacci O, Schneich C. Degradation Mechanisms of Polysorbate 20 Differentiated by (18)O-labeling and Mass Spectrometry. Pharm Res. 2017;34(1):84-100.

Zhang S, Xiao H, Molden R, Qiu H, Li N. Rapid polysorbate 80 degradation by liver carboxylesterase in a monoclonal antibody formulated drug substance at early stage development. Journal of Pharmaceutical Sciences. 2020;109(11):3300-7.

* cited by examiner

POLYSORBATE MIXTURES HAVING MODIFIED FATTY ACID ESTER DISTRIBUTION

CROSS-REFERENCE TO RELATED APPLICATIONS

This application claims priority to U.S. Provisional Application No. 63/082,606, filed on Sep. 24, 2020, and U.S. Provisional Application No. 63/082,611, filed on Sep. 24, 2020, and U.S. Provisional Application No. 63/168,567, filed on Mar. 31, 2021, the disclosures of each of which are hereby incorporated by reference in their entireties.

FIELD

The present disclosure provides polysorbate 20 compositions with particular fatty acid ester concentrations. In some embodiments, they may be used in pharmaceutical formulations, for example, to improve stability.

BACKGROUND

Polysorbate 20 (PS20) is a nonionic surfactant used in protein formulations, for example, to mitigate interfacial stresses. PS20 is a heterogeneous mixture in which a main constituent is polyoxyethylene (POE) sorbitan monolaurate. The structure contains a hydrophilic sorbitan ring attached to four branched polyoxyethylene chains, one of which has a hydrophobic laurate ester linkage. Amphiphilic properties allow PS20 to interact with liquid-air and liquid-solid interfaces, shielding protein therapeutics from agitation-induced aggregation that may occur during shipping or administration. The fatty acid ester regions of PS20 are hydrophobic and less soluble in aqueous solution than the sorbitan ring or POE chains.

PS20 compositions have a distribution of fatty acid esters that vary based on POE chain length and the core sugar structure. In addition, each of the four POE chains of PS20 can be esterified with a fatty acid, leading to mono-ester and higher order ester (HOE) (di-, tri-, and up to tetra-ester) versions of PS20 in the mixture. Fatty acid ester specifications of PS20 are set by the various pharmacopeia as shown in Table A below.

TABLE A

| Exemplary Fatty Acid Ester Content of Polysorbate 20 | | |
|---|---|---|
| Fatty Acid Ester | Composition (%) | No. of carbons |
| Caproic | ≤1 | 6 |
| Caprylic | ≤10 | 8 |
| Capric | ≤10 | 10 |
| Lauric | 40-60 | 12 |
| Myristic | 14-25 | 14 |
| Palmitic | 7-15 | 16 |
| Stearic | ≤7 | 18 |
| Oleic | ≤11 | 18:1 |
| Linolenic | ≤3 | 18:3 |

PS20 can hydrolytically degrade in biopharmaceutical drug products, causing the appearance of visible and subvisible particles. Enzymes (for example, lipases, esterases, etc.) are believed to cleave PS20 at the ester bond resulting in the formation of free fatty acids (FFAs) and free head groups or polyols. FFAs are poorly soluble in aqueous solutions and may result in visible or sub-visible particle formation either more frequently or earlier in drug product manufacture and storage with substantial implications to long-term protein stability and drug product shelf life.

SUMMARY

The present disclosure provides PS20 formulations with particular fatty acid ester distributions. In some embodiments, the polysorbate formulations herein may be less susceptible to particle formation by degradation that results in free fatty acids. The present disclosure also relates to formulations comprising the polysorbates. In some embodiments, these may help to lengthen the shelf life of pharmaceutical formulations and/or reduce waste caused by degraded and expired formulations.

Additional objects and advantages will be set forth in part in the description which follows, and in part will be obvious from the description, or may be learned by practice. The objects and advantages will be realized and attained by means of the elements and combinations particularly pointed out in the appended claims. It is to be understood that both the foregoing general description and the following detailed description are exemplary and explanatory only and are not restrictive of the claims.

The present invention provides, inter alia, compositions of PS20 with particular fatty acid ester distributions that may be less susceptible to particle formation by degradation that results in free fatty acids, and pharmaceutical formulations containing these PS20 compositions. The disclosure herein includes, for example, embodiments such as the following:

Embodiment 1 is a polysorbate 20 composition comprising fatty acid esters comprising 1% or less caproate, greater than 2.3% and less than or equal to 10% caprylate, greater than 2.8% and less than or equal to 10% caprate, greater than 52.1% and less than or equal to 60% laurate, greater than or equal to 14% and less than 18.3% myristate, greater than or equal to 7% and less than 11.9% palmitate, and less than 6.4% stearate.

Embodiment 2 is the composition of embodiment 1, comprising greater than 2.5%, or greater than 3.5%, or greater than 4%, or greater than or equal to 4.6%, and less than or equal to 10% of caprylate.

Embodiment 3 is the composition of embodiment 1 or 2, comprising greater than 3%, or greater than 3.5%, or greater than 4%, or greater than or equal to 4.4%, and less than or equal to 10% caprate.

Embodiment 4 is the composition of any one of the previous embodiments, comprising greater than 53%, greater than 55%, greater than 57%, greater than or equal to 58% and less than or equal to 60% laurate.

Embodiment 5 is the composition of any one of the previous embodiments, comprising greater than or equal to 14% and less than 18%, or less than 17%, or less than 16.5%, or less than or equal to 16.1% myristate.

Embodiment 6 is the composition of any one of the previous embodiments, comprising greater than or equal to 7% and less than 11%, or less than 10%, or less than 9.5%, or less than or equal to 8.9% palmitate.

Embodiment 7 is the composition of any one of the previous embodiments, comprising less than 6% or less than 5% or less than 1% stearate.

Embodiment 8 is the composition of any one of the previous embodiments, comprising no detectable stearate.

Embodiment 9 is the composition of any one of the previous embodiments, comprising 1% or less caproate, about 4.6% caprylate, about 4.4% caprate, about 58% laurate, about 16.1% myristate, about 8.9% palmitate, and no detectable stearate.

Embodiment 10 is the composition of any one of the previous embodiments, comprising 1% or less caproate, from 4.2% to 5.1% caprylate, from 4.0% to 4.8% caprate, from 52% to 60% laurate, from 14.5% to 17.7% myristate, from 8.0% to 9.8% palmitate, and no detectable stearate.

Embodiment 11 is the composition of any one of the previous embodiments, comprising 1% or less caproate, from 4.4% to 4.8% caprylate, from 4.2% to 4.6% caprate, from 55% to 60% laurate, from 15.3% to 16.9% myristate, from 8.5% to 9.3% palmitate, and no detectable stearate.

Embodiment 12 is the composition of any one of the previous embodiments, comprising 1% or less caproate, from 4.5% to 4.7% caprylate, from 4.3% to 4.5% caprate, from 56.8% to 59.1% laurate, from 15.8% to 16.4% myristate, from 8.7% to 9.1% palmitate, and no detectable stearate.

Embodiment 13 is a pharmaceutical formulation comprising a drug and a pharmaceutically acceptable excipient, wherein the pharmaceutically acceptable excipient comprises:
  a polysorbate 20 composition comprising fatty acid esters, wherein the fatty acid esters of the polysorbate 20 composition comprise: 1% or less caproate, greater than 2.3% and less than or equal to 10% caprylate, greater than 2.8% and less than or equal to 10% caprate, greater than 52.1% and less than or equal to 60% laurate, greater than or equal to 14% and less than 18.3% myristate, greater than or equal to 7% and less than 11.9% palmitate, and less than 6.4% stearate.

Embodiment 14 is the pharmaceutical formulation of embodiment 13, wherein the polysorbate 20 composition is from 0.01% to 0.2% (w/v) of the formulation.

Embodiment 15 is the pharmaceutical formulation of embodiment 13 or 14, wherein the drug is a protein, an antibody, an antibody fragment, an enzyme, or a peptide.

Embodiment 16 is the pharmaceutical formulation of embodiment 15, wherein the drug is a protein.

Embodiment 17 is the pharmaceutical formulation of embodiment 15, wherein the drug is an antibody.

Embodiment 18 is the pharmaceutical formulation of any of one of embodiments 13 to 17, wherein the concentration of drug is from 0.1% to 30% (w/v).

Embodiment 19 is the pharmaceutical formulation of embodiment 18, wherein the concentration of drug is from 5% to 20% (w/v).

Embodiment 20 is the pharmaceutical formulation of any of one of embodiments 13 to 19, wherein the polysorbate 20 composition is from 0.01% to 0.12%, from 0.01% to 0.08%, from 0.03% to 0.1%, or from 0.04% to 0.07%, (w/v) of the formulation.

Embodiment 21 is the pharmaceutical formulation of any of one of embodiments 13 to 20, wherein the polysorbate 20 composition is about 0.01%, 0.02%, 0.03%, 0.04%, 0.05%, 0.06%, 0.07%, 0.08%, 0.09%, 0.10%, 0.11%, or 0.12% (w/v) of the formulation.

Embodiment 22 is the pharmaceutical formulation of any of one of embodiments 13 to 21, wherein the polysorbate 20 composition is about 0.06% (w/v) of the formulation.

Embodiment 23 is the pharmaceutical formulation of any of one of embodiments 13 to 22, wherein the pH is from 4 to 8, or from 5 to 7.5, or from 6.5 to 7.5, or from 6.8 to 7.2.

Embodiment 24 is the pharmaceutical formulation of any of one of embodiments 13 to 23, wherein the pharmaceutically acceptable excipient further comprises water, an alcohol, a sugar, a buffer, a surfactant, a stabilizer, or combinations thereof.

Embodiment 25 is the pharmaceutical formulation of any of one of embodiments 13 to 24, wherein the fatty acid esters of the polysorbate 20 composition comprise greater than 2.5%, or greater than 3.5%, or greater than 4%, or greater than or equal to 4.6%, and less than or equal to 10% of caprylate.

Embodiment 26 is the pharmaceutical formulation of any of one of embodiments 13 to 25, wherein the fatty acid esters of the polysorbate 20 composition comprise greater than 3%, or greater than 3.5%, or greater than 4%, or greater than or equal to 4.4%, and less than or equal to 10% caprate.

Embodiment 27 is the pharmaceutical formulation of any of one of embodiments 13 to 26, wherein the fatty acid esters of the polysorbate 20 composition comprise greater than 53%, greater than 55%, greater than 57%, greater than or equal to 58% and less than or equal to 60% laurate.

Embodiment 28 is the pharmaceutical formulation of any of one of embodiments 13 to 27, wherein the fatty acid esters of the polysorbate 20 composition comprise greater than or equal to 14% and less than 18%, or less than 17%, or less than 16.5%, or less than or equal to 16.1% myristate.

Embodiment 29 is the pharmaceutical formulation of any of one of embodiments 13 to 28, wherein the fatty acid esters of the polysorbate 20 composition comprise greater than or equal to 7% and less than 11%, or less than 10%, or less than 9.5%, or less than or equal to 8.9% palmitate.

Embodiment 30 is the pharmaceutical formulation of any of one of embodiments 13 to 29, wherein the fatty acid esters of the polysorbate 20 composition comprise less than 6% or less than 5% or less than 1% stearate.

Embodiment 31 is the pharmaceutical formulation of any of one of embodiments 13 to 30, wherein the fatty acid esters of the polysorbate 20 composition comprise no detectable stearate.

Embodiment 32 is the pharmaceutical formulation of any of one of embodiments 13 to 31, wherein the fatty acid esters of the polysorbate 20 composition comprise 1% or less caproate, about 4.6% caprylate, about 4.4% caprate, about 58% laurate, about 16.1% myristate, about 8.9% palmitate, and no detectable stearate.

Embodiment 33 is a polysorbate 20 composition comprising fatty acid esters comprising 1.0% or less caproate, greater than or equal to 2.6% and less than or equal to 6.6% caprylate, greater than or equal to 2.4% and less than or equal to 6.4% caprate, greater than or equal to 55.0% and less than or equal to 60.0% laurate, greater than or equal to 14.1% and less than or equal to 18.1% myristate, greater than or equal to 7.0% and less than or equal to 10.9% palmitate, and less than or equal to 2.0% stearate.

Embodiment 34 is the composition of embodiment 33, comprising greater than or equal to 3%, or greater than or equal to 3.5%, or greater than or equal to 4%, or greater than or equal to 4.6%, and less than or equal to 6.6% of caprylate.

Embodiment 35 is the composition of embodiment 33 or 34, comprising greater than or equal to 2.6%, or greater than or equal to 3%, or greater than or equal to 3.5%, or greater than or equal to 4%, or greater than or equal to 4.4%, and less than or equal to 6.4% caprate.

Embodiment 36 is the composition of any one of embodiments 33 to 35, comprising greater than or equal to 56%, greater than or equal to 57%, greater than or equal to 58% and less than or equal to 60% laurate.

Embodiment 37 is the composition of any one of embodiments 33 to 36, comprising greater than or equal to 14.1% and less than or equal to 18%, or less than or equal to 17%, or less than or equal to 16%, or less than or equal to 15% myristate.

Embodiment 38 is the composition of any one of embodiments 33 to 37, comprising greater than or equal to 7% and less than 10.9%, or less than or equal to 10%, or less than or equal to 9%, or less than or equal to 8% palmitate.

Embodiment 39 is the composition of any one of embodiments 33 to 38, comprising less than or equal to 2% or less than or equal to 1.5% or less than or equal to 1% stearate.

Embodiment 40 is the composition of any one of embodiments 33 to 39, comprising no detectable stearate.

Embodiment 41 is the composition of embodiment 33, comprising 1% or less caproate, about 4.6% caprylate, about 4.8% caprate, about 57.0% laurate, about 16.2% myristate, about 9.4% palmitate, and no detectable stearate.

Embodiment 42 is the composition of embodiment 33, comprising 1% or less caproate, from 3.7% to 5.2% caprylate, from 3.7% to 5.2% caprate, from 56.3% to 57.2% laurate, from 15.9% to 16.9% myristate, from 8.8% to 9.7% palmitate, and no detectable stearate.

Embodiment 43 is the composition embodiment 33, comprising 1% or less caproate, from 3.5% to 5.5% caprylate, from 3.5% to 5.5% caprate, from 55% to 58% laurate, from 15% to 17.5% myristate, from 8.5% to 10% palmitate, and about 0.1% stearate or less.

Embodiment 44 is the composition of any one of embodiments 33 to 43, further comprising, greater than or equal to 5.8% and less than or equal to 9.8% oleate, and less than or equal to 2.0% linoleate.

Embodiment 45 is a pharmaceutical formulation comprising a drug and a pharmaceutically acceptable excipient, wherein the pharmaceutically acceptable excipient comprises:
a polysorbate 20 composition comprising fatty acid esters, wherein the fatty acid esters of the polysorbate 20 composition comprise: 1.0% or less caproate, greater than or equal to 2.6% and less than or equal to 6.6% caprylate, greater than or equal to 2.4% and less than or equal to 6.4% caprate, greater than or equal to 55.0% and less than or equal to 60.0% laurate, greater than or equal to 14.1% and less than or equal to 18.1% myristate, greater than or equal to 7.0% and less than or equal to 10.9% palmitate, and less than or equal to 2.0% stearate.

Embodiment 46 is the pharmaceutical formulation of embodiment 45, wherein the polysorbate 20 composition is from 0.01% to 0.2% (w/v) of the formulation.

Embodiment 47 is the pharmaceutical formulation of embodiment 45 or 46, wherein the drug is a protein, an antibody, an antibody fragment, an enzyme, or a peptide.

Embodiment 48 is the pharmaceutical formulation of embodiment 47, wherein the drug is a protein.

Embodiment 49 is the pharmaceutical formulation of embodiment 47, wherein the drug is an antibody.

Embodiment 50 is the pharmaceutical formulation of any of one of embodiments 45 to 49, wherein the concentration of drug is from 0.1% to 30% (w/v).

Embodiment 51 is the pharmaceutical formulation of embodiment 50, wherein the concentration of drug is from 5% to 20% (w/v).

Embodiment 52 is the pharmaceutical formulation of any of one of embodiments 45 to 51, wherein the polysorbate 20 composition is from 0.01% to 0.12%, from 0.01% to 0.08%, from 0.03% to 0.1%, or from 0.04% to 0.07%, (w/v) of the formulation.

Embodiment 53 is the pharmaceutical formulation of any of one of embodiments 45 to 52, wherein the polysorbate 20 composition is about 0.01%, 0.02%, 0.03%, 0.04%, 0.05%, 0.06%, 0.07%, 0.08%, 0.09%, 0.10%, 0.11%, or 0.12% (w/v) of the formulation.

Embodiment 54 is the pharmaceutical formulation of any of one of embodiments 45 to 53, wherein the polysorbate 20 composition is about 0.06% (w/v) of the formulation.

Embodiment 55 is the pharmaceutical formulation of any of one of embodiments 45 to 54, wherein the pH is from 4 to 8, or from 5 to 7.5, or from 6.5 to 7.5, or from 6.8 to 7.2.

Embodiment 56 is the pharmaceutical formulation of any of one of embodiments 45 to 55, wherein the pharmaceutically acceptable excipient further comprises water, an alcohol, a sugar, a buffer, a surfactant, a stabilizer, or combinations thereof.

Embodiment 57 is the pharmaceutical formulation of any of one of embodiments 45 to 56, wherein the fatty acid esters of the polysorbate 20 composition comprise greater than or equal to 3%, or greater than or equal to 3.5%, or greater than or equal to 4%, or greater than or equal to 4.6%, and less than or equal to 6.6% of caprylate.

Embodiment 58 is the pharmaceutical formulation of any one of embodiments 45 to 57, wherein the fatty acid esters of the polysorbate 20 composition comprises greater than or equal to 2.6%, or greater than or equal to 3%, or greater than or equal to 3.5%, or greater than or equal to 4%, or greater than or equal to 4.4%, and less than or equal to 6.4% caprate.

Embodiment 59 is the pharmaceutical formulation of any one of embodiments 45 to 58, wherein the fatty acid esters of the polysorbate 20 composition comprise greater than or equal to 56%, greater than or equal to 57%, greater than or equal to 58% and less than or equal to 60% laurate.

Embodiment 60 is the pharmaceutical formulation of any one of embodiments 45 to 59, wherein the fatty acid esters of the polysorbate 20 composition comprise greater than or equal to 14.1% and less than or equal to 18%, or less than or equal to 17%, or less than or equal to 16%, or less than or equal to 15% myristate.

Embodiment 61 is the pharmaceutical formulation of any one of embodiments 45 to 60, wherein the fatty acid esters of the polysorbate 20 composition comprise greater than or equal to 7% and less than 10.9%, or less than or equal to 10%, or less than or equal to 9%, or less than or equal to 8% palmitate.

Embodiment 62 is the pharmaceutical formulation of any one of embodiments 45 to 61, wherein the fatty acid esters of the polysorbate 20 composition comprise less than or equal to 2% or less than or equal to 1.5% or less than or equal to 1 stearate.

Embodiment 63 is the pharmaceutical formulation of any one of embodiments 45 to 62, wherein the fatty acid esters of the polysorbate 20 composition comprise no detectable stearate.

Embodiment 64 is the pharmaceutical formulation of any one of embodiments 45 to 63, wherein the fatty acid esters of the polysorbate 20 composition comprise 1% or less caproate, about 4.6% caprylate, about 4.8% caprate, about 57.0% laurate, about 16.2% myristate, about 9.4% palmitate, and no detectable stearate.

Embodiment 65 is the pharmaceutical formulation of any one of embodiments 45 to 63, wherein the fatty acid esters of the polysorbate 20 composition comprise 1% or less caproate, from 3.7% to 5.2% caprylate, from 3.7% to 5.2% caprate, from 56.3% to 57.2% laurate, from 15.9% to 17.0% myristate, from 8.8% to 9.8% palmitate, and no detectable stearate.

Embodiment 66 is the pharmaceutical formulation of any one of embodiments 45 to 63, wherein the fatty acid esters of the polysorbate 20 composition comprise 1% or less caproate, from 3.5% to 5.5% caprylate, from 3.5% to 5.5% caprate, from 55% to 58% laurate, from 15% to 17.5% myristate, from 8.5% to 10% palmitate, and about 0.1% stearate or less.

Embodiment 67 is the pharmaceutical formulation of any one of embodiments 45 to 66, wherein the fatty acid esters of the polysorbate 20 composition further comprises, greater than or equal to 5.8% and less than or equal to 9.8% oleate, and less than or equal to 2.0% linoleate.

Embodiment 68 is the formulation of any one of embodiments 45 to 67, comprising fewer free fatty acid particles resulting from degradation of fatty acid esters when compared to a formulation comprising a standard polysorbate 20 composition that is subjected to the same storage conditions.

Embodiment 69 is the formulation of any one of embodiments 45 to 68, further comprising a higher order ester degrading drug product, wherein up to 10% more fatty acid esters may be degraded to free fatty acids before free fatty acid particle formation is observed than in an HOE degrading drug product formulation comprising a standard polysorbate 20 composition that otherwise has the identical contents and is stored under the same conditions.

Embodiment 70 is the formulation of any one of embodiments 45 to 69, wherein the number of free fatty acid particles produced by metal nucleation of free fatty acids is less than the number of free fatty acid particles produced by metal nucleation of free fatty acids in a formulation comprising a standard polysorbate 20 composition that is otherwise identical in content and storage conditions.

Embodiment 71 is the composition or formulation of any one of embodiments 33 to 70, wherein free fatty acids are produced by hydrolytic and/or oxidative degradation of the fatty acid esters.

Embodiment 72 is the composition or formulation of any one of embodiments 33 to 70, wherein degradation of fatty acid esters results in free fatty acid particle formation that is delayed relative to free fatty acid particle formation in a composition or formulation comprising a standard polysorbate 20 composition.

Embodiment 73 is the composition or formulation of embodiment 72, wherein the free fatty acid particles are visible.

Embodiment 74 is the composition or formulation of embodiment 72, wherein the free fatty acid particles are subvisible.

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims. The accompanying drawings, which are incorporated in and constitute a part of this specification, illustrate several exemplary embodiments and together with the description, serve to explain certain principles described herein.

BRIEF DESCRIPTION OF THE DRAWINGS

FIG. 4A shows the effect of CALB on Modified HP PS20 lot 1. FIG. 4B shows the effect of PCL on Modified HP PS20 lot 1. FIG. 4C shows the effect of CALB on HP PS20 control. FIG. 4D shows the effect of PCL on HP PS20 control. Monoesters elute early between 5 and 15 minutes and higher-order (di- and tri-) esters elute between 15 and 20 minutes. CALB preferentially degrades monoesters and PCL primarily targets higher order esters of PS20.

FIG. 5A shows CALB degraded Modified HP PS20 and HP PS20. FIG. 5B shows PCL degraded Modified HP PS20.

FIG. 7A shows the effect of mAb-B on Modified HP PS20 lot 1; FIG. 7B shows the effect of mAb-C on Modified HP PS20 lot 1; FIG. 7C shows the effect of mAb-D on Modified HP PS20 lot 1; FIG. 7D shows the effect of mAb-B on control lot HP PS20; FIG. 7E shows the effect of mAb-C on control lot HP PS20; FIG. 7F shows the effect of mAb-D on control lot HP PS20. Monoesters elute early between 12 and 22 minutes and higher order esters (diesters and triesters) elute between 22 and 30 minutes.

FIGS. 8A-C show visible particles and the subvisible slurry, identified as free fatty acids, from the mAb-B arm of the real-time 5° C. stability study measured at 14 weeks.

FIG. 8A shows images of particles from mAb-B Modified HP PS20 lot 1 and FIG. 8B shows images of particles from mAb-B modified HP PS20. FIG. 8C shows normalized absorbance spectra (arbit units) of the filtered particles using FT-IR spectroscopy. Similar results were obtained for mAb-C and mAb-D (data not shown).

FURTHER DESCRIPTION OF EXEMPLARY EMBODIMENTS

A. Definitions

Unless otherwise defined, scientific and technical terms used in connection with the present disclosure shall have the meanings that are commonly understood by those of ordinary skill in the art. Further, unless otherwise required by context, singular terms shall include pluralities and plural terms shall include the singular.

In this application, the use of "or" means "and/or" unless stated otherwise. In the context of a multiple dependent claim, the use of "or" refers back to more than one preceding independent or dependent claim in the alternative only. Also, terms such as "element" or "component" encompass both elements and components comprising one unit and elements and components that comprise more than one subunit unless specifically stated otherwise.

As described herein, any concentration range, percentage range, ratio range or integer range is to be understood to include the value of any integer within the recited range and, when appropriate, fractions thereof (such as one tenth and one hundredth of an integer), unless otherwise indicated.

Units, prefixes, and symbols are denoted in their Système International de Unites (SI) accepted form. Numeric ranges are inclusive of the numbers defining the range. Measured values are understood to be approximate, taking into account significant digits and the error associated with the measurement.

As used herein, percentages ("%") of PS20 in a formulation are weight to volume ("w/v") percentages unless specified otherwise. And percentages ("%") of individual fatty acids within a PS20 composition, unless specifically stated otherwise, are peak area percentages in a gas chromatogram as determined using the USP/EP method for measuring composition of fatty acids in PS20 compositions.

Figure 1:
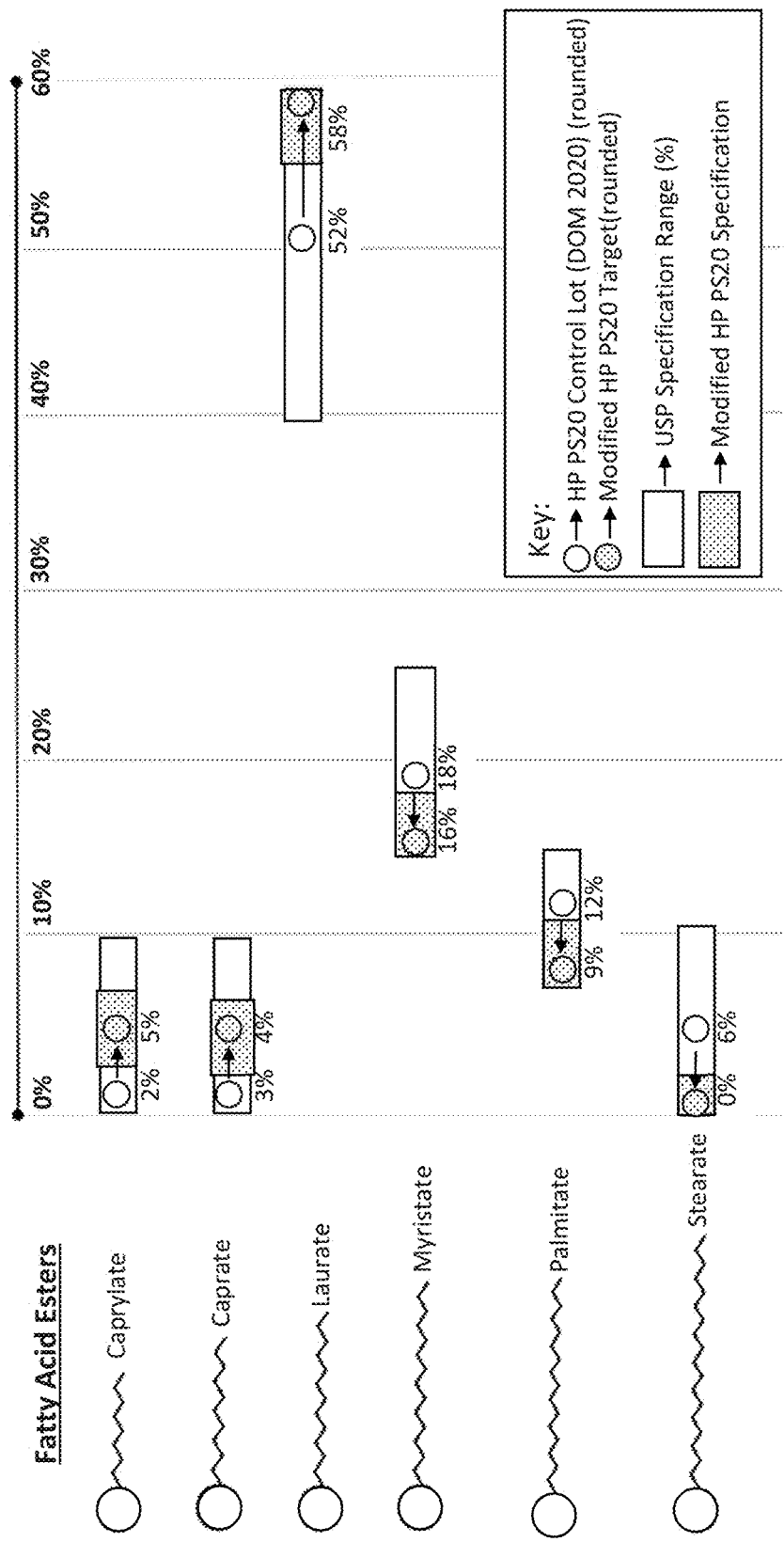
FIG. 1 shows the fatty acid ester (FAE) specifications of Modified HP PS20 (in the dotted rectangular area) shown as a subset of the USP specification ranges (in open rectangular area). FAE target levels of Modified HP PS20 are shown in circles with dots and FAE levels of the HP PS20 control lot is shown in open circles.

As used herein, "polysorbate 20" or "PS20" refers to a polysorbate-type nonionic surfactant that is formed by the ethoxylation of sorbitan before the addition of lauric acid. Polysorbate 20 (PS20) can be used, for example, to prevent aggregation biopharmaceuticals in pharmaceutical or other types of formulations. PS20 is a structurally variable mixture or distribution of different fatty acid esters wherein each of the fatty acid esters may be a monoester or a higher order ester, HOE. A "standard PS20 composition" is a polysorbate 20 lot that meets the pharmacopoeia standards (see, e.g., Table A above) but does not meet the specifications disclosed herein, for example, as provided in FIG. 1 herein. HP PS20 is an example of a standard PS20.

As used herein, "fatty acid ester" refers to a type of ester that results from the combination of a fatty acid with an alcohol, where a fatty acid is a carboxylic acid with a long aliphatic chain, which is either saturated or unsaturated. Fatty acids may have an unbranched chain of an even number of carbon atoms, for example, from 4 to 28.

As used herein, "free fatty acid" or "FFA" refers to the long aliphatic chain moiety of the fatty acid ester. FFAs are produced, for example, by the degradation of fatty acid esters. Free fatty acids may remain solubilized or may aggregate to form aggregates or particles.

As used herein, "caproic acid," also known as hexanoic acid, refers to the carboxylic acid derived from hexane with the chemical formula $CH_3(CH_2)_4COOH$. This acid has a carbon chain length of six (C6). Salts and esters of decanoic acid are called "caproates."

As used herein, "caprylic acid" also known as octanoic acid, refers to a saturated fatty acid, and a carboxylic acid, with the structural formula $CH_3(CH_2)_6COOH$. This acid has a carbon chain length of eight (C8). Salts and esters of decanoic acid are called "caprylates."

As used herein, "capric acid" also known as decanoic acid or decylic acid, refers to a saturated fatty acid with the formula $CH_3(CH_2)_8COOH$. This acid has a carbon chain length of 10 (C10). Salts and esters of decanoic acid are called "decanoates" or "caprates."

As used herein, "lauric acid" also known as dodecanoic acid, refers to a saturated fatty acid with the formula $CH_3(CH_2)_{10}COOH$. This acid has a carbon chain length of twelve (C12). The salts and esters of lauric acid are known as "laurates."

As used herein, "myristic acid" refers to a saturated fatty acid with the molecular formula $CH_3(CH_2)_{12}COOH$. This acid has a carbon chain length of fourteen (C14). Its salts and esters are commonly referred to as "myristates" or "tetradecanoates."

As used herein, "palmitic acid" also known as hexadecanoic acid, refers to a saturated fatty acid with the chemical formula $CH_3(CH_2)_{14}COOH$. This acid has a carbon chain length of sixteen (C16). Salts and esters of decanoic acid are called "palmitates."

As used herein, "stearic acid" also known as octadecanoic acid, refers to a saturated fatty acid with the chemical formula $CH_3(CH_2)_{16}COOH$. This acid has a carbon chain length of eighteen (C18). The salts and esters of stearic acid are called "stearates."

As used herein, "oleic acid" refers to a fatty acid with the chemical formula $CH_3(CH_2)_7CH=CH(CH_2)_7COOH$. This acid has a carbon chain length of eighteen carbon atoms one point of unsaturation (C18:1). The salts and esters of stearic acid are called "oleates."

As used herein, "linoleic acid" refers to a saturated fatty acid with the chemical formula $COOH(CH_2)_7CH=CHCH_2CH=CH(CH_2)_4CH_3$. This acid has a carbon chain length of eighteen carbon atoms and two points of unsaturation (C18:2). The salts and esters of stearic acid are called "linoleates."

Figure 2:
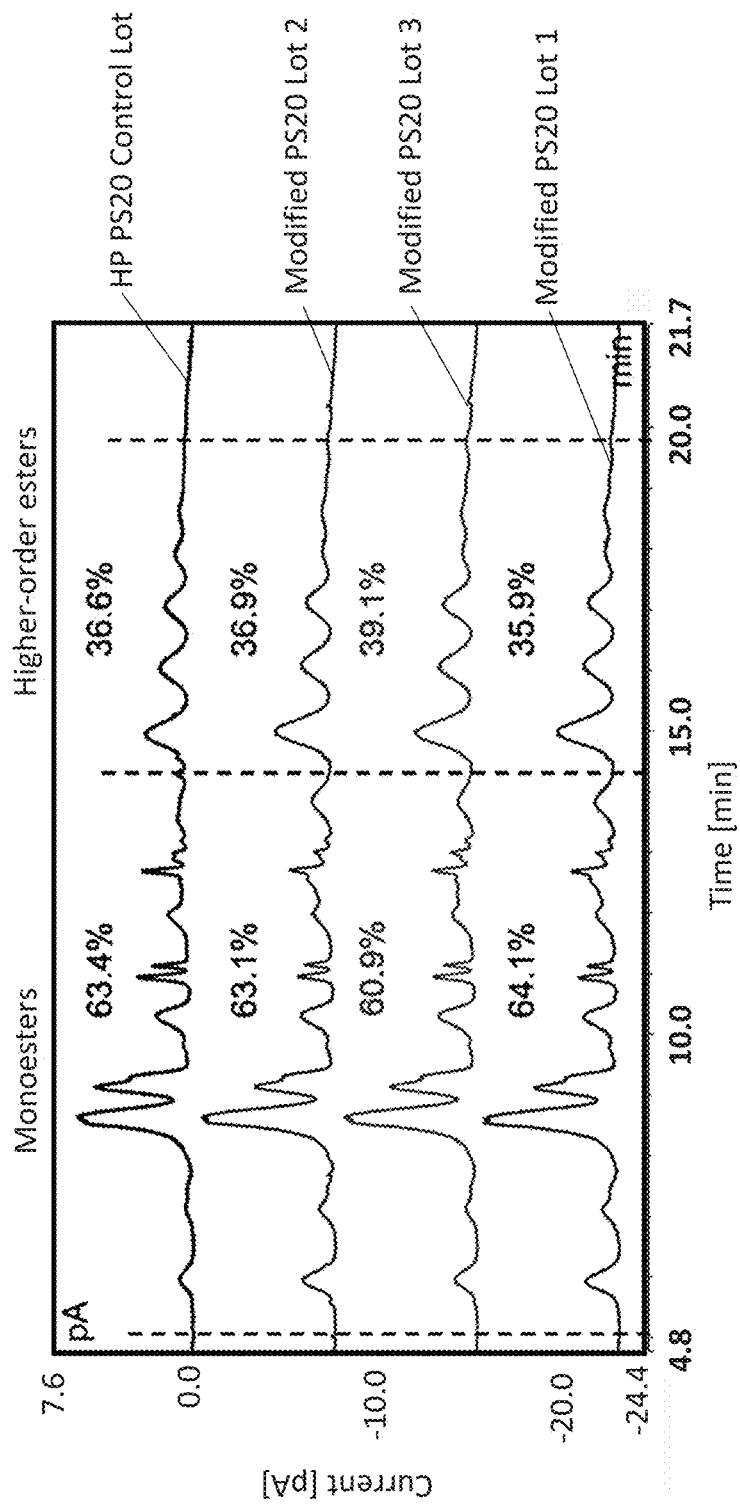
FIG. 2 shows ester distribution of neat PS20 measured by reversed phase UHPLC. Monoesters elute early between 5 and 15 minutes and higher-order (di- and tri-) esters (HOE) elute between 15 and 20 minutes.

As used herein, "higher order ester" refers to di-, tri-, and up to tetra-ester versions of the polyoxyethylene chains of polysorbate 20, as opposed to a "monoester" form, which has one. Each of the four polyoxyethylene chains of polysorbate 20 can be esterified with a fatty acid, leading to mono-ester and higher order esters in the mixture. The higher order ester (HOE) polysorbate 20 species can have any combination of fatty acid esters and are not restricted to just one type of fatty acid ester per molecule. Each sorbitan ring may be ethoxylated with approximately 20 molar equivalents. Additionally, the polysorbate 20 head group may be either a sorbitan or isosorbide ring, the latter resulting in only two polyoxyethylene chains that may be esterified with a fatty acid. The HOE content of a PS20 composition can be quantified using a polysorbate ester distribution assay. (See e.g., FIG. 2).

As used herein, "higher order ester degrading drug product" or an "HOE degrading drug product" refers to any drug product that causes the HOE peak area in the PS20 to decrease over time relative to the monoester peak area in an ultra-high performance reversed phase liquid chromatography assay, as identified using a polysorbate ester distribution assay. (See e.g., FIG. 2 and FIGS. 7A-F)

As used herein, "aggregate" and "aggregation" means to come together or collect in a mass or whole, e.g., as in the aggregation of free fatty acid chains. Aggregated free fatty acid chains may also be referred to herein as particles or as FFA particles. Aggregates can be self-aggregating or aggregate due to other factors, e.g., presence of aggregating agents, precipitating agents, agitation, or other means and methods that cause free fatty acid chains to come together. A compound that is "susceptible to aggregation" is one that has been observed to aggregate with other molecules, especially upon agitation. Aggregation may be observed visually, such as when a previously clear formulation in solution becomes cloudy or contains precipitates, or by methods such as size exclusion chromatography (SEC), which separates molecules by size. Aggregation may result in subvisible FFA particles which may be quantified using light obscuration or flow imaging microscopy.

As used herein, "drug" refers to any kind of active ingredient used in pharmaceutical formulations. A drug may be, for example, comprise a protein, such as an antibody, an antibody fragment, an enzyme, or a peptide.

The terms "protein" refers to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, proteins containing one or more analogs of an amino acid (including, for example, unnatural amino acids, etc.), as well as other modifications known in the art.

The term "antibody" as used herein includes monoclonal antibodies (including full length antibodies which have an immunoglobulin Fc region), antibody compositions with polyepitopic specificity, multispecific antibodies (e.g., bispecific antibodies, diabodies, and single-chain molecules, as well as antigen-binding fragments (e.g., Fab, F(ab')$_2$, and Fv). The term "antibody" includes "antibody fragments" and "antigen binding fragments." An "antibody fragment" or "antigen binding fragment" comprises a portion of an intact antibody that includes the antigen binding portion and/or the variable region of the intact antibody, and that binds specifically to the antigen. Examples of antibody fragments include Fab, Fab', F(ab')$_2$ and Fv fragments; diabodies; linear antibodies (see U.S. Pat. No. 5,641,870, Example 2; Zapata et al., *Protein Eng.* 8(10): 1057-1062 [1995]); single-chain antibody molecules and multispecific antibodies formed from antibody fragments.

As used herein, "an enzyme" refers to any protein that catalyzes a chemical reaction. The catalytic function of an enzyme constitutes its activity or enzymatic activity. An enzyme typically is classified according to the type of catalytic function it carries out, e.g., hydrolysis of peptide bonds.

A "formulation" refers to a mixture of ingredients that may comprise PS20, among other ingredients, such as a protein, a buffer, a stabilizer, etc. In some cases, a formulation is a liquid solution, such as an aqueous solution, while in other cases it may be lyophilized. The term "pharmaceutical formulation" or "therapeutic formulation" or "therapeutic preparation" or like terms refers to a preparation or composition comprising at least one active ingredient and at least one additional component or excipient substance, and which is in such form as to permit the biological activity of the active ingredient to be effective in a mammalian subject, and which is "suitable for therapeutic use" or "suitable for pharmaceutical use," meaning that the formulation as a whole is not unacceptably toxic to a mammalian subject and does not contain components which are unacceptably toxic to a mammalian subject to which the formulation would be administered or which are at concentrations that would render them unacceptably toxic to a subject.

As used herein, a "stable" formulation is one which retains its physical and/or chemical stability upon storage. Stability can be measured at a selected temperature for a selected time period. The extent of particle formation, such as visible and/or subvisible particle formulation, or the extent of aggregation, or the extent of formation of degradation products, or any combination of these factors, during storage may be used as an indicator of stability, for example.

Increasing the "stability" of a drug-containing formulation may involve reducing (as compared to an unmodified drug-containing formulation) or preventing the formation of aggregates in that formulation; or reducing or preventing the formation of visible and/or subvisible particles in that formulation; or reducing or preventing of degradation products of components of the formulation so that other components may continue act so as to maintain the stability of the drug.

The term "stabilizer" refers to agents that stabilize large, charged biomolecules, such as proteins and antibodies. In some cases, a surfactant or tonicity agent may act as a stabilizer.

As used herein, a "surfactant" refers to a surface-active agent, preferably a nonionic surfactant. Examples of surfactants herein include polysorbate (for example, polysorbate 20 and, polysorbate 80); poloxamer (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.); polyethyl glycol, polypropyl glycol, and copolymers of ethylene and propylene glycol (e.g. Pluronics, PF68 etc.); etc.

The term "tonicity agent" refers to an agent that is used to adjust or maintain the relative concentration of solutions. Examples of tonicity agents include polyhydric sugar alcohols, such as trihydric or higher sugar alcohols, such as glycerin, erythritol, arabitol, xylitol, sorbitol and mannitol.

As used herein, "buffer" refers to a solution that resists changes in pH by the action of its acid-base conjugate components.

A "sterile" formulation is aseptic or free or essentially free from all living microorganisms and their spores.

B. PS20 Compositions

Without wishing to be bound by any particular theory, PS20 compositions with higher concentrations of longer-chain fatty acid esters of myristate (C14), palmitate (C16), and stearate (C18:0) in PS20 may be more susceptible to the formation of visible and sub-visible particles. Degradation of fatty acid esters results in the formation of free fatty acids (FFA). PS20 compositions comprising less longer-chain fatty acid esters may therefore be less susceptible to visible and sub-visible FFA particle formation.

In some embodiments, the PS20 compositions provided herein comprise lower concentrations of stearate, palmitate, and myristate esters while remaining within USP/EP/JP specifications. In some embodiments the stearate ester level may be reduced from ~5-6% in commercially available formulations to ~0%. In some embodiments, the concentration of short chain fatty acid esters (i.e. fatty acid esters with carbon chain length C6, C8, C10, and C12) is enriched while the long chain fatty acid esters (i.e. fatty acid esters with carbon chain length C14, C16, and C18) are minimized or diluted.

Provided herein are polysorbate 20 compositions comprising 1% or less caproate, greater than 2.3% and less than or equal to 10% caprylate, greater than 2.8% and less than or equal to 10% caprate, greater than 52.1% and less than or equal to 60% laurate, greater than or equal to 14% and less than 18.3% myristate, greater than or equal to 7% and less than 11.9% palmitate, and less than 6.4% stearate.

In some embodiments, the composition comprises greater than 2.5%, or greater than 3.5%, or greater than 4%, or greater than or equal to 4.6%, and less than or equal to 10% of caprylate.

In some embodiments, the composition comprises greater than 3%, or greater than 3.5%, or greater than 4%, or greater than or equal to 4.4%, and less than or equal to 10% caprate.

In some embodiments, the composition comprises greater than 53%, greater than 55%, greater than 57%, greater than or equal to 58% and less than or equal to 60% laurate.

In some embodiments, the composition comprises greater than or equal to 14% and less than 18%, or less than 17%, or less than 16.5%, or less than or equal to 16.1% myristate.

In some embodiments, the composition comprises greater than or equal to 7% and less than 11%, or less than 10%, or less than 9.5%, or less than or equal to 8.9% palmitate.

In some embodiments, the composition comprises less than 6% or less than 5% or less than 1% stearate.

In some embodiments, the composition comprises no detectable stearate.

In some embodiments, provided herein are polysorbate 20 compositions comprising fatty acid esters comprising 1.0% or less caproate, greater than or equal to 2.6% and less than or equal to 6.6% caprylate, greater than or equal to 2.4% and less than or equal to 6.4% caprate, greater than or equal to 55.0% and less than or equal to 60.0% laurate, greater than or equal to 14.1% and less than or equal to 18.1% myristate, greater than or equal to 7.0% and less than or equal to 10.9% palmitate, and less than or equal to 2.0% stearate.

In some embodiments, the composition comprises greater than or equal to 3%, or greater than or equal to 3.5%, or greater than or equal to 4%, or greater than or equal to 4.6%, and less than or equal to 6.6% of caprylate.

In some embodiments, the composition comprises greater than or equal to 2.6%, or greater than or equal to 3%, or greater than or equal to 3.5%, or greater than or equal to 4%, or greater than or equal to 4.4%, and less than or equal to 6.4% caprate.

In some embodiments, the composition comprises greater than or equal to 56%, greater than or equal to 57%, greater than or equal to 58% and less than or equal to 60% laurate.

In some embodiments, the composition comprises greater than or equal to 14.1% and less than or equal to 18%, or less than or equal to 17%, or less than or equal to 16%, or less than or equal to 15% myristate.

In some embodiments, the composition greater than or equal to 7% and less than 10.9%, or less than or equal to 10%, or less than or equal to 9%, or less than or equal to 8% palmitate.

In some embodiments, the composition comprises less than or equal to 2% or less than or equal to 1.5% or less than or equal to 1% stearate. In some embodiments, the composition comprises no detectable stearate. The composition of claim 1, comprising 1% or less caproate, about 4.6% caprylate, about 4.8% caprate, about 57.0% laurate, about 16.2% myristate, about 9.4% palmitate, and no detectable stearate.

In some embodiments, the composition comprises 1% or less caproate, from 3.7% to 5.2% caprylate, from 3.7% to 5.2% caprate, from 56.3% to 57.2% laurate, from 15.9% to 17.0% myristate, from 8.8% to 9.8% palmitate, and no detectable stearate.

In some embodiments, the composition comprises 1% or less caproate, from 3.5% to 5.5% caprylate, from 3.5% to 5.5% caprate, from 55% to 58% laurate, from 15% to 17.5% myristate, from 8.5% to 10% palmitate, and about 0.1% stearate or less.

In some embodiments, the composition further comprises further, greater than or equal to 5.8% and less than or equal to 9.8% oleate, and less than or equal to 2.0% linoleate.

In some embodiments, the composition comprises 1% or less caproate, about 4.6% caprylate, about 4.4% caprate, about 58% laurate, about 16.1% myristate, about 8.9% palmitate, and no detectable stearate.

In some embodiments, the composition comprises 1% or less caproate, from 4.2% to 5.1% caprylate, from 4.0% to 4.8% caprate, from 52% to 60% laurate, from 14.5% to 17.7% myristate, from 8.0% to 9.8% palmitate, and no detectable stearate.

In some embodiments, the composition comprises 1% or less caproate, from 4.4% to 4.8% caprylate, from 4.2% to 4.6% caprate, from 55% to 60% laurate, from 15.3% to 16.9% myristate, from 8.5% to 9.3% palmitate, and no detectable stearate.

In some embodiments, the composition comprises 1% or less caproate, from 4.5% to 4.7% caprylate, from 4.3% to 4.5% caprate, from 56.8% to 59.1% laurate, from 15.8% to 16.4% myristate, from 8.7% to 9.1% palmitate, and no detectable stearate.

C. Formulations

Also provided herein are pharmaceutical formulations comprising at least one drug and at least one pharmaceutically acceptable excipient, wherein the pharmaceutically acceptable excipient comprises a polysorbate 20 composition comprising fatty acid esters as described above. Thus, in some formulations, the formulation comprises a polysorbate 20 composition in which the fatty acid esters comprise 1% or less caproate, greater than 2.3% and less than or equal to 10% caprylate, greater than 2.8% and less than or equal to 10% caprate, greater than 52.1% and less than or equal to 60% laurate, greater than or equal to 14% and less than 18.3% myristate, greater than or equal to 7% and less than 11.9% palmitate, and less than 6.4% stearate of the polysorbate 20 composition. In other formulations, the formulation comprises a polysorbate 20 composition comprising fatty acid esters, wherein the fatty acid esters of the polysorbate 20 composition comprise: 1.0% or less caproate, greater than or equal to 2.6% and less than or equal to 6.6% caprylate, greater than or equal to 2.4% and less than or equal to 6.4% caprate, greater than or equal to 55.0% and less than or equal to 60.0% laurate, greater than or equal to 14.1% and less than or equal to 18.1% myristate, greater than or equal to 7.0% and less than or equal to 10.9% palmitate, and less than or equal to 2.0% stearate.

In some embodiments, one or more additional pharmaceutically acceptable excipients are included. In other embodiments, the formulation consists essentially of the at least one drug and the polysorbate 20 composition.

In some embodiments, the at least one drug comprises a protein, such as an antibody, an antibody fragment, an enzyme, or a peptide.

In some embodiments of the pharmaceutical formulation, the concentration of drug is from 0.1% to 30% (w/v) of the formulation, such as from 1% to 30%, 5% to 30%, 5% to 25%, 5% to 20%, 5% to 10%, 10% to 30%, 10% to 25%, 10% to 20%, or 15% to 25%.

In pharmaceutical formulations herein, a total surfactant concentration may be from 0.001% to 1%, from 0.001% to 0.5%, from 0.005% to 0.2%, from 0.01% to 0.1%, or from 0.02% to 0.06%, or 0.03% to 0.05%. In some embodiments, the total surfactant concentration is from 0.01% to 1% (w/v) of the formulation, such as 0.01% to 0.5%, 0.01% to 0.25%, 0.01% to 0.12%, or 0.01% to 0.2%. In pharmaceutical formulations herein, the polysorbate 20 concentration may be from 0.001% to 1%, from 0.005% to 0.2%, from 0.01% to 0.1%, or from 0.02% to 0.06%, or 0.03% to 0.05%. In some embodiments, the polysorbate 20 composition is from 0.01% to 1% (w/v) of the formulation, such as 0.01% to 0.5%, 0.01% to 0.25%, 0.01% to 0.12%, or 0.01% to 0.2%.

In some embodiments of the pharmaceutical formulation, the polysorbate 20 composition comprises from 0.01% to 0.2%, from 0.01% to 0.12%, from 0.01% to 0.08%, from 0.03% to 0.1%, or from 0.04% to 0.07%, (w/v) of the formulation.

In some embodiments of the pharmaceutical formulation, the polysorbate 20 composition comprises about 0.01%, 0.02%, 0.03%, 0.04%, 0.05%, 0.06%, 0.07%, 0.08%, 0.09%, 0.10%, 0.11%, or 0.12% (w/v) of the formulation.

In some embodiments of the pharmaceutical formulation, the polysorbate 20 composition is about 0.06% (w/v) of the formulation.

In some embodiments of the pharmaceutical formulation, the pH is from 4 to 8, or from 5 to 7.5, or from 6.5 to 7.5, or from 6.8 to 7.2.

In some embodiments, the polysorbate 20 composition in the pharmaceutical formulation comprises greater than 2.5%, or greater than 3.5%, or greater than 4%, or greater than or equal to 4.6%, and less than or equal to 10% of caprylate.

In some embodiments, the polysorbate 20 composition in the pharmaceutical formulation comprises greater than or equal to 3%, or greater than or equal to 3.5%, or greater than or equal to 4%, or greater than or equal to 4.6%, and less than or equal to 6.6% of caprylate.

In some embodiments, the polysorbate 20 composition in the pharmaceutical formulation comprises greater than 3%, or greater than 3.5%, or greater than 4%, or greater than or equal to 4.4%, and less than or equal to 10% caprate.

In some embodiments, the polysorbate 20 composition in the pharmaceutical formulation comprises greater than or equal to 2.6%, or greater than or equal to 3%, or greater than or equal to 3.5%, or greater than or equal to 4%, or greater than or equal to 4.4%, and less than or equal to 6.4% caprate.

In some embodiments, the polysorbate 20 composition in the pharmaceutical formulation comprises greater than 53%, greater than 55%, greater than 57%, greater than or equal to 58% and less than or equal to 60% laurate.

In some embodiments, the polysorbate 20 composition in the pharmaceutical formulation comprises greater than or equal to 56%, greater than or equal to 57%, greater than or equal to 58% and less than or equal to 60% laurate.

In some embodiments, the polysorbate 20 composition in the pharmaceutical formulation comprises greater than or equal to 14% and less than 18%, or less than 17%, or less than 16.5%, or less than or equal to 16.1% myristate.

In some embodiments, the polysorbate 20 composition in the pharmaceutical formulation comprises greater than or equal to 14.1% and less than or equal to 18%, or less than or equal to 17%, or less than or equal to 16%, or less than or equal to 15% myristate.

In some embodiments, the polysorbate 20 composition in the pharmaceutical formulation comprises greater than or equal to 7% and less than 11%, or less than 10%, or less than 9.5%, or less than or equal to 8.9% palmitate.

In some embodiments, the polysorbate 20 composition in the pharmaceutical formulation comprises greater than or equal to 7% and less than 10.9%, or less than or equal to 10%, or less than or equal to 9%, or less than or equal to 8% palmitate.

In some embodiments, the polysorbate 20 composition in the pharmaceutical formulation comprises less than 6% or less than 5% or less than 1% stearate. In some embodiments, the polysorbate 20 composition in the pharmaceutical formulation comprises less than or equal to 2%, or less than or equal to 1.5%, or less than or equal to 1% stearate. In some embodiments, the polysorbate 20 composition in the pharmaceutical formulation comprises no detectable stearate.

In some embodiments, the polysorbate 20 composition in the pharmaceutical formulation comprises 1% or less caproate, about 4.6% caprylate, about 4.4% caprate, about 58% laurate, about 16.1% myristate, about 8.9% palmitate, and no detectable stearate.

In some embodiments, the polysorbate 20 composition in the pharmaceutical formulation comprises 1% or less caproate, about 4.6% caprylate, about 4.8% caprate, about 57.0% laurate, about 16.2% myristate, about 9.4% palmitate, and no detectable stearate.

In some embodiments, the polysorbate 20 composition in the pharmaceutical formulation comprises 1% or less caproate, from 3.7% to 5.2% caprylate, from 3.7% to 5.2% caprate, from 56.3% to 57.2% laurate, from 15.9% to 17.0% myristate, from 8.8% to 9.8% palmitate, and no detectable stearate.

In some embodiments, the polysorbate 20 composition in the pharmaceutical formulation comprises 1% or less caproate, from 3.5% to 5.5% caprylate, from 3.5% to 5.5% caprate, from 55% to 58% laurate, from 15% to 17.5% myristate, from 8.5% to 10% palmitate, and about 0.1% stearate or less.

In some embodiments, the polysorbate 20 composition in the pharmaceutical formulation further comprises, greater than or equal to 5.8% and less than or equal to 9.8% oleate, and less than or equal to 2.0% linoleate.

In some embodiments of the pharmaceutical formulation, the pharmaceutically acceptable excipient further comprises water, an alcohol, a sugar, a buffer, a surfactant, a stabilizer, or combinations thereof. In some embodiments, the aqueous formulations comprising the PS20 compositions disclosed herein may further comprise one or more excipients chosen from a stabilizer, a buffer, a surfactant, and a tonicity agent. An aqueous formulation of the invention can be prepared in a pH-buffered solution. Buffers useful in the formulations disclosed herein may have a pH in the range from about pH 4.5 to about 9.0. In certain embodiments the pH is in the range from about pH 4.5 to about 7.0, in the range from about pH 4.5 to about 6.5, in the range from about pH 4.5 to about 6.0, in the range from about pH 4.5 to about 5.5, in the range from about pH 4.5 to about 5.0, in the range from about pH 5.0 to about 7.0, in the range from about pH 5.5 to about 7.0, in the range from about pH 5.7 to about 6.8, in the range from about pH 5.8 to about 6.5, in the range from about pH 5.9 to about 6.5, in the range from about pH 6.0 to about 6.5, or in the range from about pH 6.2 to about 6.5. In certain embodiments, the liquid formulation has a pH in the range of about 4.7 to about 5.2, in the range of about 5.0 to 6.0, or in the range of about 5.2 to about 5.8.

Examples of buffers that may control the pH within this range include organic and inorganic acids and salts thereof. For example, acetate (e.g., histidine acetate, arginine acetate, sodium acetate), succinate (e.g., histidine succinate, arginine succinate, sodium succinate), gluconate, phosphate, fumarate, oxalate, lactate, citrate, and combinations thereof. The buffer concentration can be from about 1 mM to about 600 mM, depending, for example, on the buffer and the desired isotonicity of the formulation.

Additional surfactants can optionally be added to the pharmaceutical formulation. Exemplary additional surfactants include nonionic surfactants such as poloxamers (e.g. poloxamer 188, etc.). A total amount of surfactant may be added such that it may reduce aggregation of the formulated drug and/or minimizes the formation of particulates in the formulation and/or reduces adsorption, for example.

Tonicity agents can be present in any amount between 0.1% to 25% by weight, or between 1% to 5% by weight, taking into account the relative amounts of the other ingredients. Exemplary tonicity agents include polyhydric sugar alcohols, such as trihydric or higher sugar alcohols, such as glycerin, erythritol, arabitol, xylitol, sorbitol and mannitol.

In some embodiments, the formulation is a pharmaceutical formulation for in vivo administration. In some embodiments, the formulation is sterile. In some embodiments, the formulation is freeze-dried. In some embodiments, the formulation is stored in liquid, solution form. In some embodiments, the formulation is stored in concentrated form and diluted prior to use. The formulation may be rendered sterile by filtration through sterile filtration membranes, for example. The therapeutic formulations herein can be placed into a sterile container such as a container having a sterile access port, for example, an intravenous solution bag or vial having a stopper pierceable by a hypodermic injection needle.

D. Methods of Making and Testing PS20 Compositions and PS20 Containing Formulations Certain compositions of commercially available PS20 have been found to degrade early in the storage period (e.g., T<400 days), in some cases resulting in undesirable visible and subvisible particles in formulations comprising the PS20.

Polysorbate 20 compositions with concentrations of stearate, palmitate, and myristate esters described herein, and within USP/EP/JP specifications, may be made using process known in the art.

Methods of determining the distribution of fatty acid esters can be found, for example, in the European Pharmacopeia 10.0 rev 01/2017:0426: Polysorbate 20 at page 3589-3590. That document describes methods for determining the composition of fatty acids in PS20 (2.4.22, Method C), for example. Methods may also be found in the Interim Revision Announcement of the USP (Official Sep. 1, 2014) Polysorbate 20 section, referencing Fats and Fixed Oils (401), Fatty Acid Composition.

Methods for determining free fatty acid concentrations may be found, for example, in Tomlinson A, et al. *Molecular pharmaceutics*. 2015; 12(11):3805-15).

Stability of the PS20-containing compositions can be measured using known methods, including, for example, visualization and/or imaging of visible and subvisible particles using commercially available particle counters. For example, aggregation may be assessed by size exclusion chromatography. And tests such as agitation over several hours can be conducted, followed by size exclusion chromatography or visual inspection. For example, in some embodiments, agitation at 100 rpm for several hours, such as for 24 hours may be used to determine the extent of aggregates or particulates in a formulation.

In some cases, compositions provided herein may be assayed for presence of visible and sub-visible particles. In one embodiment, visible particles may be observed by placing the sample in a glass vial and rotating the sample in the presence of a Tyndall light. In one embodiment, subvisible particles are analyzed using a high accuracy (HIAC) particle counter. In some embodiments, the HIAC instrument may be configured to a 10 mL/min flow rate, 0.1 mL tare volume, and 0.4 mL sample volume. In particular embodiments, the samples may be analyzed using 4 runs of 0.4 mL sips, with the first run of each sample was discarded to prevent measurement error due to sample carryover. Filter sizes of 2, 5, 10, 15, and 25 microns can be used for analysis.

In some embodiments, PS20 compositions can be analyzed by determining, for example, fatty acid ester distribution, acid value, hydroxyl value, saponification value, percent water content. These values may then be compared to relevant US Pharmacopoeia and/or European Pharmacopoeia and/or Japanese Pharmacopeia specifications. A shallow gradient assay can be performed to determine mono-, di-, and tri-ester content. Free fatty acid (FFA) levels in a PS20 composition are determined by fatty acid mass spectrometry. Metal ion content can be tested by inductively coupled plasma mass spectroscopy (ICP-MS). Metal ions such as aluminum and calcium can cause free fatty acid nucleation and increase the oxidation potential of PS20.

The following functional and stability studies may also be performed on PS20 lots.

A vial agitation test may show the ability of a PS20 to protect proteins when exposed to agitation stress in a vial. In one method, a test protein in a buffer solution is used as an agitation sensitive molecule prone to aggregation at air water interfaces. A PS20 composition is added in at increasing concentrations, such as of 0.02% to 0.08%. Samples are agitated on an arm shaker at 70 rpm at room temperature for 24 hours. Static controls are placed beside the instrument during this time. Each of the samples is analyzed by size exclusion ultra high performance liquid chromatography (SE-UHPLC) to examine protein aggregation and particle formation in the agitated and control samples.

A small scale IV bag agitation test may also be performed. The purpose of this test is to model the concentration of PS20 needed to protect products after a drug product has been removed from the vial and diluted in an IV bag prior to infusion. In this test a test protein is diluted in saline with various concentrations of PS20 and agitated, for example, on an orbital shaker at 180 RPM for 2 hours at 5° C. with the static control being refrigerated at 5° C. for 2 hours. The same indicators as the vial agitation test (sub-visible/visible particle formation and aggregation) are analyzed post agitation in saline. The concentration of PS20 below which aggregation and/or particles are observed can be determined, to establish comparability or improvement in terms of interfacial protection in IV bags. For example, aggregation can be assessed as above using SE-UHPLC.

The oxidation liability of a PS20 material may also be tested. A histidine acetate placebo formulated with 0.2% w/v PS20 can be tested, for example, at 40° C. for 1 month. The primary mechanism of degradation of PS20 in this test is expected to be oxidative. Oxidative degradation of PS20 is accelerated in placebo formulations at stress temperatures of 40° C. since there is no protein present to quench peroxides. A 10 mM methionine arm may be added to the test to ensure that the oxidative degradation of the PS20 is mitigated by the platform stabilizer. Loss of PS20 determined in a mixed mode evaporative light scattering detector (ELSD) is used as a measure of oxidative degradation.

A stability test at 5° C. for 3 months, for example, in the presence of agents known to degrade PS20, can also be used to understand PS20 degradation, FFA generation and particle formation propensity of a PS20 containing formulation. Molecules may be added that have been shown to degrade PS20 and that are expected to cause FFA particles to form within 3 months at 5° C. FFA concentration and aggregation and particle formation may be assessed during the test, such as each week for 12 weeks, by the techniques described above. An enzyme-based PS20 degradation test may be performed to assess the propensity of a PS20 composition to form FFA and associated particles. For example, *Candida antarctica* lipase B (CALB) specifically degrades mono-esters while *Pseudomonas cepacia* lipase (PCL) specially degrades higher order esters.

By adding each of these enzymes separately to a PS20 composition, and analyzing PS20 concentration and sub-visible particle formation over time, FFA particle formation can be monitored.

Enzyme working solutions of CALB and PCL can be prepared, for example, by dissolving free enzyme into 20 mM histidine acetate buffer at approximately 0.01 U/mL and 12.5 U/mL respectively to ensure particle formation occurs within ~3 hours. 10% PS20 is then added into these enzyme solutions to a final concentration of 0.1% w/v. The solution is divided into multiple 15 cc vials with a 10 mL fill volume. PS20 concentration by mixed-mode ELSD and sub-visible particles by HIAC is measured at time zero and every 30 minutes thereafter for a total of 180 minutes.

In any of the above analyses, PS20 compositions according to the disclosure herein may, for example, be compared to PS20 compositions that meet the broader, pharmacopoeia standards (see, e.g., Table A above) but do not meet the specifications disclosed herein ("standard PS20"). Modified HP PS20 is an example of a PS20 composition according to the present disclosure. HP PS20 is an example of a standard PS20.

In some embodiments, in the PS20 compositions, or formulations containing PS20 compositions, disclosed herein, the degradation of fatty acid esters results in free fatty acid particle formation that is delayed relative to free fatty acid particle formation in a composition or formulation that is otherwise identical in content and storage conditions but that comprises a standard polysorbate 20 composition.

In some embodiments, a formulation comprising PS20 is provided wherein the formulation comprises fewer free fatty acid particles resulting from degradation of fatty acid esters when compared to a formulation that comprises a standard polysorbate 20 composition but that is otherwise identical in contents and that is subjected to the same storage conditions.

In some embodiments, the formulations disclosed herein further comprise a higher order ester (HOE) degrading drug product. In some embodiments comprising an HOE degrading drug product, when the claimed PS20 composition is used, up to 10% more esterified fatty acids may be degraded to free fatty acids before free fatty acid particle formation is observed than in an HOE degrading drug product formulation comprising a standard polysorbate 20 composition that otherwise has the identical contents and under the same storage conditions. An HOE degrading drug product is a drug product that causes the HOE peak area in the PS20 to decrease over time, as identified using a polysorbate ester distribution assay.

In some embodiments, in the PS20 compositions, or formulations containing PS20 compositions, disclosed herein, the number of particles produced by metal nucleation of free fatty acids that is less than the number of particles produced by metal nucleation of free fatty acids in a composition of standard polysorbate 20 or a formulation comprising a standard polysorbate 20 composition that is otherwise identical in content and storage conditions.

In some embodiments, the PS20 compositions, or formulations containing PS20 compositions, disclosed herein, have fewer particles produced by metal nucleation of free fatty acids than the number of particles produced by metal nucleation of free fatty acids in a composition of standard polysorbate 20 or a formulation comprising a standard polysorbate 20 composition that is otherwise identical in content and storage conditions.

E. Kits

In another embodiment of the invention, kits for reducing polysorbate degradation are provided. In some embodiments, a kit comprising any of the PS20 compositions provided herein is provided. In one embodiment, such kits comprise at least one PS20 compositions provided herein, a drug, and at least one pharmaceutically acceptable excipient and instructions for preparing a pharmaceutically acceptable formulation as provided herein.

F. Models

Each of the four POE chains of PS20 can be esterified with a fatty acid, leading to mono-ester and higher order ester (HOE) (di-, tri-, and up to tetra-ester) versions of PS20 in the mixture. The higher order ester (HOE) PS20 species can have any combination of fatty acid esters; they are not restricted to just one type of fatty acid ester per molecule. Each sorbitan ring is ethoxylated with approximately 20 molar equivalents. Additionally, the PS20 head group may be either a sorbitan or isosorbide ring, the latter resulting in only two POE chains that may be esterified with a fatty acid[14, 30, 31].

Without wishing to be bound by any particular theory, PS20 compositions with lower concentrations of higher order esters may be more susceptible to the formation of visible and sub-visible particles. Degradation of fatty acid esters results in the formation of free fatty acids (FFA). Higher order esters may facilitate dissolution of FFAs in formulations comprising PS20.

In one aspect, the present disclosure also provides a method that could be used, for example, to predict free fatty acid particle formation in a composition comprising polysorbate 20 (PS20). Such a method comprises, for example:
a. determining the pH of the composition;
b. determining the PS20 concentration in the composition; and
c. determining the higher order ester to total peak area fraction of PS20; and
d. calculating the solubility of free fatty acid esters in the composition using the following equation $$(\beta_1 + \beta_1 \times 10^{pH-\beta_2}) \times \frac{289.5*[PS20] - 12.7*HOE + ([PS20] - 0.04)*((HOE - 0.5)*306.8) - 4.1}{12.8}$$

where $\beta_1$ is the solubility of the non-ionized fatty acid, $\beta_2$ is the experimentally determined pKa, [PS20] is the PS20 concentration in the composition, and HOE is the higher order ester to total peak area fraction of PS20.

The invention will be more fully understood by reference to the following examples, which should not be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

EXAMPLES

Example 1. Characterization and Testing of PS20 Compositions

The following experiments compared the susceptibility of two types of PS20 compositions to formation of free fatty acids: one lot of HIP PS20, a standard PS20 meeting the standard pharmacopeia specifications; and three lots of Modified HP PS20, a PS20 composition meeting a narrower set of specifications as described herein. See Table 1 and FIG. 1. Experiments included testing formulations comprising the PS20 compositions for formation of free fatty acids (FFA) and associated FFA particles.

A. Materials and Methods
Reagents and Materials
Monoclonal antibodies (mAbs) A, B, C and D are CHO-derived monoclonal antibodies obtained from Genentech Inc. (South San Francisco, CA). MAbs-B and C are of the IgG1 subclass whereas mAb-D is of the IgG4 subclass. The mAbs were purified by a series of chromatography steps including Protein A affinity chromatography and ion-exchange chromatography. MAb-A and B were formulated at 30 mg/mL in a low ionic strength histidine hydrochloride buffer whereas mAbs-C and D were formulated at 150 and 180 mg/mL, respectively, in a high ionic strength arginine succinate buffer without surfactants or other excipients, unless specified otherwise. The pH of the mAb formulations ranged from 5.5-6.0. Tween™ 20 High Purity (HP PS20) and Tween™ 20 Modified High Purity (Modified HP PS20) were purchased from Croda (Edison, NJ). L-histidine, L-arginine and histidine hydrochloride were obtained from Ajinomoto (Raleigh, NC). Sodium acetate, sodium chloride and glacial acetic acid were purchased from JT Baker (Phillipsburg, NJ). Dansyl-L-methionine cyclohexylammonium salt was purchased from Santa Cruz Biotechnology (Dallas, TX). The enzymes *Mucor miehei* lipase (MML), *Candida antarctica* lipase (CAL), *Pseudomonas cepacia* lipase (PCL) and *Candida antarctica* lipase B (CALB) as well as L-methionine, aluminum chloride hexahydrate and glutaraldehyde were purchased from Sigma Aldrich (St. Louis, MO). ReliZyme™ HA403/M beads were obtained from Resindion S.r.l. (Binasco, Italy). Ultrapure water from an Elga PURELAB® (Woodridge, IL) system was used for the preparation of aqueous solutions. Borosilicate glass vials of different sizes used in the stability studies were purchased from Schott AG (Mainz, Germany) with corresponding sizes of Daikyo D777-1 stoppers from West Pharmaceutical Services (Lionville, Pennsylvania). Polyethylene terephthalate copolyeste (PETG) screw-top vials of different sizes were purchased from Thermo Fisher Scientific (Waltham, MA).

B. Assays
Polysorbate 20 Concentration
PS20 was quantified by mixed-mode high performance liquid chromatography (HPLC) equipped with an evaporative light scattering detector (ELSD) adapted from the method described in Hewitt et al. (1). The instrument parameters, column, gradient and mobile phases used were identical to those described in our previous work (2).

Polysorbate 20 Ester Distribution
PS20 ester distribution in samples containing protein was evaluated using a two-dimensional liquid chromatography (2DLC) system setup similar to the one used by Li et al. (3). An Agilent 1290 Infinity 2DLC system was coupled with a Corona Ultra charged aerosol detector (CAD) operated at a nitrogen pressure of 35 psi. A mixed-mode method (first dimension) was used to remove protein coupled with a reversed phase method (second dimension) to study the composition of PS20 esters. The PS20 esters that eluted from the mixed-mode column were trapped in a 500 μL stainless steel loop and then sent to the second dimension for further separation of the esters subspecies. The first dimension used an Oasis MAX column (20 mm×2.1 mm, 30 μm) and the second dimension used an Acquity BEH C18 column (150 mm×2.1 mm, 1.7 μm). The mobile phase A and B used for the first dimension were 2% acetic acid in water and 2% acetic acid in acetonitrile, respectively. The gradient for the first dimension was as follows: 0-1 min, 2% B; 1-1.1 min, 2-20% B; 1.1-5 min, 20% B; 5-5.1 min 20-90% B; 5.1-9 min, 90% B; 9-9.1 min, 90-2% B; 9.1-13 min, 2% B. The mobile phase A and B used for the second dimension were water and 80/20 (v/v) acetonitrile/isopropanol, respectively. The gradient for the second dimension was as follows: 0-2.4 min; 5.0% B; 2.4-2.5 min, 5-45% B; 2.5-20 min, 45-100% B; 20-25 min, 100% B; 25-25.1 min, 100-5% B; 25.1-30 min, 5% B.

PS20 ester distribution in samples without protein was evaluated by reversed phase chromatography using a one-dimensional Waters Acquity Ultra-High-Performance Liquid Chromatography (UHPLC) H-Class system equipped with a Thermo Corona Ultra CAD. The column, gradient and mobile phases were identical to those used for the second dimension of the 2DLC CAD method described above.

Free Fatty Acid Quantification
Total (Soluble+Insoluble Fraction) Free Fatty Acids
Total FFAs in DP as well as PS20 raw material were detected using a reversed-phase chromatography method coupled to a mass detector as described in Honemann et al. (5). Briefly, 200 μL of a precipitation solution containing 1 μg/mL labeled FFA internal standards dissolved in 80:20 acetone:methanol was added to 50 μL samples. Samples were incubated for 1 hour at room temperature followed by two rounds of centrifugation at 15,000×g for 15 minutes at 25° C. 100 µL of supernatant was aliquoted into liquid chromatography mass spectroscopy (LC-MS) vials. The same procedure was used when analyzing FFA levels in samples with or without protein. Analysis was performed on a Waters Acquity H-Class UHPLC coupled to a Waters Qda™ mass spectrometer. The column, mobile phase, gradient and MS instrument settings were based on those described by Honemann et al. (5). Both the monoisotopic and isotopic peaks for each FFA were summed and compared to its respective internal standard for quantification. Lauric, myristic, palmitic and stearic acids were quantified.

Free Fatty Acids in the Insoluble Fraction

In order to analyze FFA distribution of the particles, observed in the DP, particles were isolated by filtration, resuspended and analyzed by reversed-phase mass spectrometry. The filtration was conducted utilizing a 10 mm inner diameter (ID) glass funnel onto a gold coated polycarbonate filter with a 0.8 µm pore size. 2.0 mL of ice-cold sample was added into the funnel and a mild vacuum pressure of 400 Torr was applied. The samples were swirled prior to sampling to ensure homogeneity. The particles isolated onto each filter were immediately resuspended in 500 µL of methanol for analysis. A formulation buffer control was also included for each DP. Each sample and control was tested with duplicate filtrations. The samples were then analyzed neat using the same gradient and LC-MS conditions described in the 'total FFA' quantification section, but were quantified against an external standard curve for lauric, myristic, palmitic and stearic acids. The FFA levels of the buffer control were subtracted from those of the corresponding DP samples.

Visual Inspection

Visual inspection was carried out against a black background and a white background using white fluorescent light between 2000 and 3750 lux at the inspection point according to USP<790> (8) and Ph. Eur. 2.9.20 (9). The vial was gently swirled and inspected for approximately 5 seconds against each of the backgrounds. A positive result was recorded when two independent analysts observed visible particles.

Enhanced Visual Inspection

Enhanced visual inspection with increased light intensity and magnification was performed using a Bosch® Table-Top model APK-51. The vial was rotated followed by visual inspection using a high resolution camera under 10× magnification and a bottom LED light. A positive result was recorded when two independent analysts observed particles.

Subvisible Particles by Light Obscuration

Cumulative subvisible particles were counted by light obscuration using a HIAC 9703+ liquid particle counting system equipped with a 3000A sampler and HRLD-150 sensor obtained from Hach. The instrument performance was verified using 5 µm polystyrene Count-CAL bead standards purchased from Thermo Fisher Scientific. Cumulative subvisible particle counts ≥2 µm, ≥5 µm, ≥10 µm and ≥25 µm were measured in the experimental samples. Four 1 mL aliquots were sampled for each measurement, and the results of the last three aliquots were averaged after discarding the first one.

Subvisible Particles by Flow Imaging Microscopy

Cumulative subvisible particle counts and morphologies were measured by flow imaging microscopy. Measurements were performed using a FlowCam® 8100 system equipped with a 10× objective, 80×700 µm flow cell, and 1 mL syringe pump, obtained from Fluid Imaging Technologies, Inc. For each measurement, 700 uL of sample was pumped through the flow cell at a flow rate of 200 uL/min. Captured images were classified by particle type (FFA, silicone oil, proteinaceous, air bubble, or miscellaneous) based on size and morphology, using previous work by Siska et al. (6) and Werk et al. (7) as guides for particle classification. All images that were classified as air bubbles were excluded from analysis.

Soluble Monoclonal Antibody Aggregation

Soluble mAb aggregation was quantified as the % sum total of all high molecular weight forms (HMWF) by size exclusion chromatography (SEC) using a Tosoh TSKgel UP-SW3000 column, 2 µm, 4.6 mm×300 mm on a Waters Acquity UHPLC H-Class Bio system. The samples were eluted at ambient temperature with 0.2 M potassium phosphate, 0.25M potassium chloride, and pH 6.2 with an isocratic flow rate of 0.3 mL/min. The elution peaks were monitored at 280 nm by an ultraviolet (UV) diode array detector.

Metal Analysis by ICP-MS

Trace metals in PS20 raw material were quantified by inductively coupled plasma mass spectrometry (ICP-MS). HP PS20 and Modified HP PS20 were diluted to 10% (w/v) in 5% nitric acid immediately before analysis to avoid acidic hydrolysis of PS20. Measurements were made with a Thermo Fisher Scientific X series II ICP-MS instrument. A small volume of each sample was dissociated into its elemental components using an argon plasma torch, which dissociates the sample into ionized elemental components that are subsequently identified by mass using conventional mass spectrometry. The detection range of the ICP-MS method used is 1-100 ppb multiplied by a sample dilution factor.

Particle Identification

Particles were isolated by gentle filtration of the DP. A filtration funnel with 4 mm inner diameter was assembled with a gold-coated polycarbonate filter with 0.8 µm pore size. Visible particles and subvisible particle slurry were isolated by filtering 0.5 ml of sample under mild vacuum (600 Torr). The captured particles were rinsed with 0.1 mL Milli-Q water and analyzed by FT-IR microscopy using a Nicolet iN10-MX Infrared Microscope. The entire filtration region containing isolated particles/slurry was captured with a ~5 mm×5 mm field-of-view mosaic. Visible particles >100 µm in length and subvisible particle slurry regions with a 150 µm×150 µm aperture were selected for identification. A 60% spectral match to a custom-built database was used to identify particles.

C. Study Design

PS20 Degradation Using Non-Immobilized Enzymes

The Modified HP PS20 lots 1, 2 and 3 and the HP PS20 control lot were each diluted in water to 10% w/v. Enzyme working solutions were prepared by dissolving non-immobilized CALB and PCL at concentrations of 0.01 U/mL and 12.5 U/mL, respectively, in a low ionic strength histidine acetate buffer at pH 5.5. To initiate the PS20 hydrolysis reaction, the 10% w/v PS20 stock solutions were spiked separately into the enzyme working solutions to a final concentration of 0.1% w/v. Samples were then placed at 5° C. in 50 cc glass vials. PS20 concentration by mixed-mode HPLC ELSD and subvisible particles by light obscuration were measured at select 5° C. time points. Subvisible particles were measured on ice cold samples since the length of the study was too short to allow for room temperature equilibrium. The HP PS20 control lot was degraded and analyzed alongside each Modified HP PS20 lot to account for day to day variability.

PS20 Degradation in Drug Product

The low ionic strength mAb-B formulation was spiked separately with the Modified HP PS20 lots 1, 2 and 3 and the HP PS20 control lot to a final concentration of 0.02% w/v. The high ionic strength mAb-C and mAb-D formulations were spiked with only the Modified HP PS20 lot 1 and the HP PS20 control lot to a final concentration of 0.02% w/v. Methionine, at 10 mM, was added as an antioxidant to all the formulations to minimize oxidative degradation of PS20. A 5 mL volume of each formulation was filled into 6 cc glass vials and placed on stability at 5° C. for 12 weeks. Five dedicated vials of each formulation were repeatedly monitored weekly for the presence of visible particles by visual inspection under a black and white background and enhanced visual inspection under increased light intensity and 10× magnification. Subvisible particles were also monitored weekly by flow imaging microscopy. Samples were equilibrated to ambient temperature prior to visible and subvisible particle measurements. Particle identification by FT-IR and FFA concentration measurements of the insoluble fraction by LC-MS were performed for each formulation after 14 weeks at 5° C. Additional material for each formulation was pulled every week and frozen at −70° C. The frozen aliquots were thawed and tested for PS20 concentration by mixed-mode HPLC ELSD, PS20 ester distribution by reversed phase UHPLC CAD and total (insoluble and soluble fraction) FFA concentration measurements by LC-MS for all conditions and time points.

Metal Nucleation of Free Fatty Acids

The enzymes *Mucor miehei* lipase (MML) and *Candida antarctica* lipase (CAL) were immobilized on ReliZyme™ HA403/M beads based on the procedure described in Graf et al. (10). Stock solutions (5% w/v in water) of the Modified HP PS20 lot 1-3 and the HP PS20 control lot were partially degraded by 10% (confirmed by mixed-mode ELSD) using each enzyme. The partially degraded PS20 stock solutions were separately spiked into a low ionic strength histidine acetate buffer at pH 5.5 containing 0-250 ppb aluminum (Al) to a nominal PS20 concentration of 0.04% w/v (0.036% w/v non-degraded PS20 and 0.004% w/v degraded PS20). Vials were stored at 5° C. and assessed for the formation of visible particles by visual inspection under a black and white background and subvisible particles using light obscuration for up to 21 days. Prior to the visual inspection, vials were allowed to equilibrate to ambient temperature for at least 4 hours. For subvisible particles, measurements were conducted using cold sample solutions to capture early changes in the particle counts. Samples containing non-degraded PS20 were included as controls.

D. Results and Discussion

To assess analytical and functional comparability, three lots of Modified HP PS20 and one lot of HP PS20 (control) were evaluated in side-by-side studies. FFA particle levels were compared for polysorbates relative to each other by performing PS20 hydrolytic degradation studies and metal nucleation studies in the presence and absence of external metal nucleation factors.

The three lots of Modified HP PS20 had lower levels of stearate, palmitate and myristate esters compared with HP PS20, as shown in Table 1. For example, the HP PS20 control lot had relatively high levels of stearate, palmitate and myristate esters at 6, 12 and 18%, respectively, compared to 0-0.1, 8.8-9.7, and 15.9-16.9, for the 3 lots of Modified HP PS20.

TABLE 1

Fatty Acid Ester Distribution and Specifications

| Fatty Acid Ester | Modified HP PS20 Lot 1 | Modified HP PS20 Lot 2 | Modified HP PS20 Lot 3 | HPPS20 Control Lot | HP PS20 Spec (USP[a]/EP[b]/ChP[c]) | Modified HP PS20 Specs[d] |
|---|---|---|---|---|---|---|
| C6:0 CaproateCaproic (%) | 0.0 | 0.0 | 0.0 | 0.0 | ≤1.0 | 0.0-1.0 |
| C8:0 CaprylateCaprylic (%) | 5.2 | 4.6 | 3.7 | 2.2 | ≤10.0 | 2.6-6.6 |
| C10:0 CaprateCapric (%) | 5.2 | 4.8 | 3.7 | 2.8 | ≤10.0 | 2.4-6.4 |
| C12:0 LaurateLauric (%) | 57.0 | 56.3 | 57.2 | 53.4 | 40.0-60.0 | 55.0-60.0 |
| C14:0 MyristateMyristic (%) | 15.9 | 16.2 | 16.9 | 18.4 | 14.0-25.0 | 14.1-18.1 |
| C16:0 PalmitatePalmitic (%) | 8.8 | 9.4 | 9.7 | 12.0 | 7.0-15.0 | 7.0-10.9 |
| C18:0 StearateStearic (%) | 0.0 | 0.0 | 0.1 | 6.0 | ≤7.0 (EP) and ≤11.0 (USP/ChP) | 0.0-2.0 |

TABLE 1-continued

Fatty Acid Ester Distribution and Specifications

| Fatty Acid Ester | Modified HP PS20 Lot 1 | Modified HP PS20 Lot 2 | Modified HP PS20 Lot 3 | HPPS20 Control Lot | HP PS20 Spec (USP[a]/EP[b]/ChP[c]) | Modified HP PS20 Specs[d] |
|---|---|---|---|---|---|---|
| C18:1 OleateOleic (%) | 7.5 | 8.7 | 8.7 | 5.2 | ≤11.0 | 5.8-9.8 |
| C18:2 LinoleateLinoleic (%) | 0.0 | 0.0 | 0.0 | 0.0 | ≤3.0 | 0.0-2.0 |

[a]United States Pharmacopeial Convention. United States Pharmacopeia and National Formulary. Rockville, MD: United States Pharmacopeial Convention; 2018.
[b]Council of Europe. European Pharmacopoeia. 9.3rd ed. Strasbourg, France: European Medicines Agency; 2017.
[c]Chinese Pharmacopoeia Commission. Chinese Pharmacopoeia. 11th ed. Beijing, China: China Medical Science Press; 2020.
[d]Modified HP PS20 specifications fall within HP PS20 compendial specifications
DOM = Date of Manufacture
Modified HP PS20 Lot 1 DOM = Jul. 8, 2020;
Modified HP PS20 Lot 2 DOM Jul. 15, 2020;
Modified HP PS20 Lot 3 DOM Jun. 19, 2020;
HP PS20 Control Lot DOM Mar. 14, 2020

Higher Order Ester Fraction

Higher order ester (HOE) fraction is an attribute of PS20 that may impact enzymatic degradation rates, FFA solubilizing capacity and surface activity. The hydrolases present in DP formulations may have varying specificities towards monoesters and HOEs of PS20; some preferentially degrade monoesters like in the DP used by Zhang et al. (4) while others may target HOEs like in the DP used by Li et al. (3). A change in the HOE fraction may impact the PS20 degradation rate of a DP depending on the specificity of degradation observed. For instance, an increase in HOE fraction may increase PS20 degradation rates in a HOE degrading DP due to higher starting level of the substrate that is cleaved by the hydrolases. In addition to degradation rates, HOE fraction directly impacts FFA solubilizing capacity of PS20 (2). The HOEs of PS20 solubilize FFAs better than an equivalent amount of monoesters. The HOE peak area fractions for Modified HP PS20 lots 1, 2 and 3 were within 4% of HP PS20. For example, the HP PS20 lot used in Doshi et al. (11) had a HOE peak area fraction of 42% whereas the lot used in Fish et al. (12) was at 36%. A previously published FFA solubility model predicts that a difference in HOE peak area fraction of <5% results in a negligible change (<3%) in FFA solubility (2). Subsequent experiments to ensure that the small differences in HOE peak area fraction do not have a significant impact the material properties.

Free Fatty Acid Levels in the PS20 Raw Material

Figure 3A:
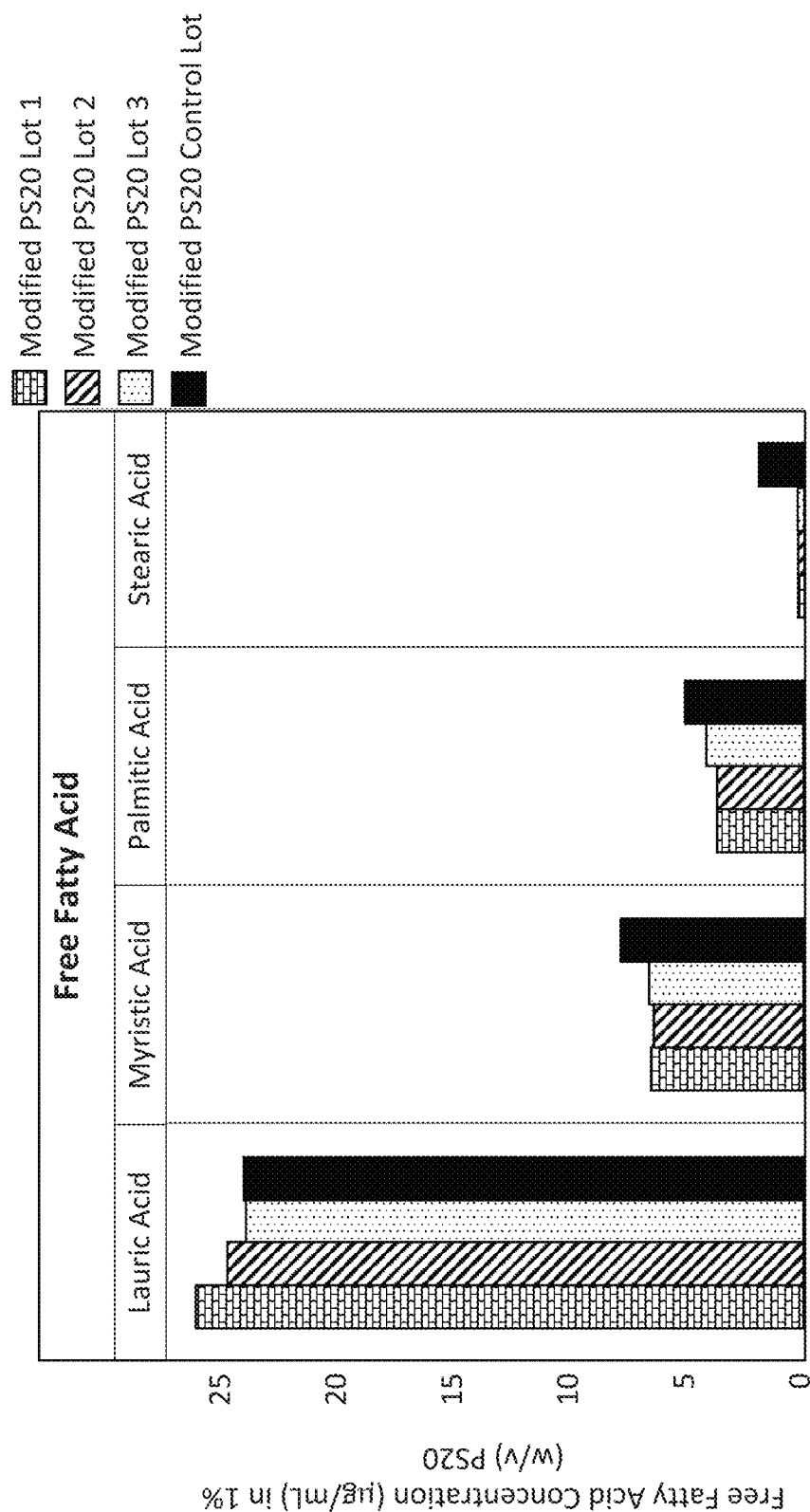
FIG. 3A shows the concentration of unbound free fatty acids (µg/mL) in the 1% PS20 from Modified HP PS20 lots 1-3 and control lot HP PS20 (w/v) as measured by reversed phase MS.

HP PS20 raw material is known to contain low, residual levels of unbound FFAs that did not undergo the esterification reaction to the polyoxyethylene (POE) chains during PS20 synthesis. It is important to compare the residual FFA levels between Modified HP PS20 and HP PS20 since they may contribute to the overall FFA particle susceptibility of each grade. The levels of stearic, myristic and palmitic acids were lower in 1% w/v Modified HP PS20 compared with 1% w/v HP PS20 while lauric acid was correspondingly higher (FIG. 3A). The FFA blend used in the synthesis of Modified HP PS20 also had lower levels of long chain FFAs and higher levels of short chain FFAs relative to HP PS20. For both Modified HP PS20 and HP PS20, the overall FFA contribution from the raw material is low relative to the aqueous solubility limits of each FFA. For instance, a previously published FFA solubility model predicts a palmitic acid solubility of ~1 ug/mL in a 0.02% w/v PS20 formulation at pH 5.5 (2). Based on those results, the PS20 raw material would contribute ~0.1 ug/mL palmitic acid in the same formulation for both polysorbates.

Trace Metal Content of the PS20 Raw Material

Figure 3B:
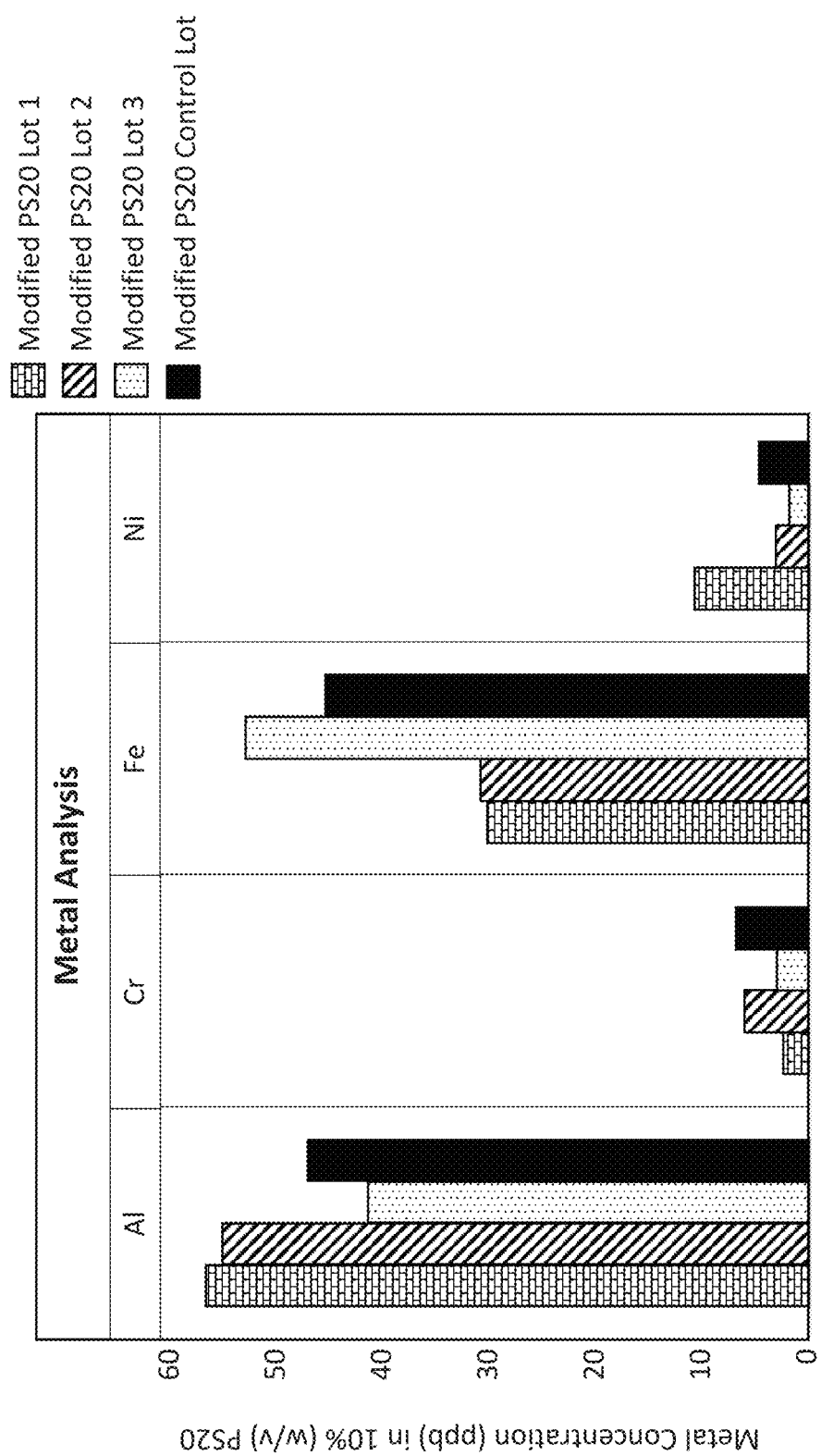
FIG. 3B shows the trace metal analysis results for the metals Al, Cr, Fe, and Ni (ppb) in 10% PS20 from Modified HP PS20 lots 1-3 and control lot HP PS20 (w/v) as measured by ICP-MS. Trace metals were measured in a 10% PS20 solution. Al, Cr, Fe and Ni levels were above the limit of quantification (LOQ) of 1 ppb, whereas other metals like copper were below LOQ.
Figure 4A:
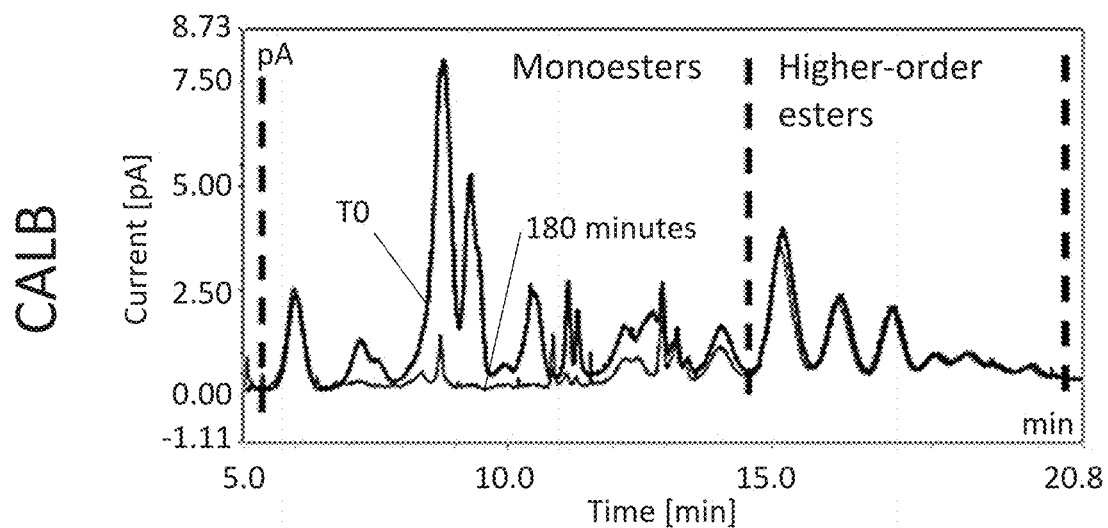
FIGS. 4A-D show the ester distribution by reversed phase UHPLC of PS20 from Modified HP PS20 lot 1 and control lot HP PS20 degraded by non-immobilized enzymes *Candida antarctica* lipase B (CALB) and *Pseudomonas cepacia* lipase (PCL).
Figure 4B:
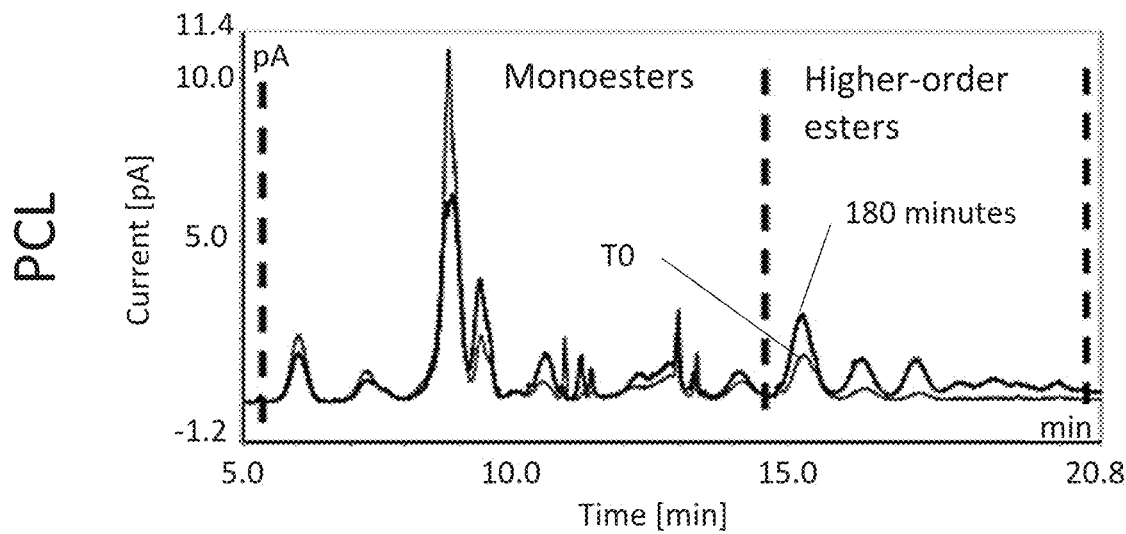
Figure 4C:
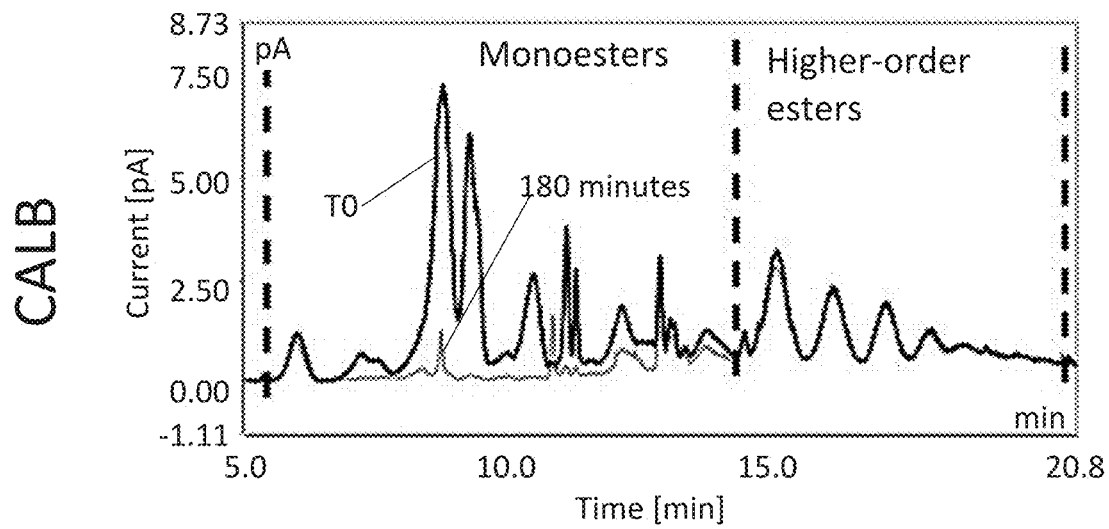
Figure 4D:
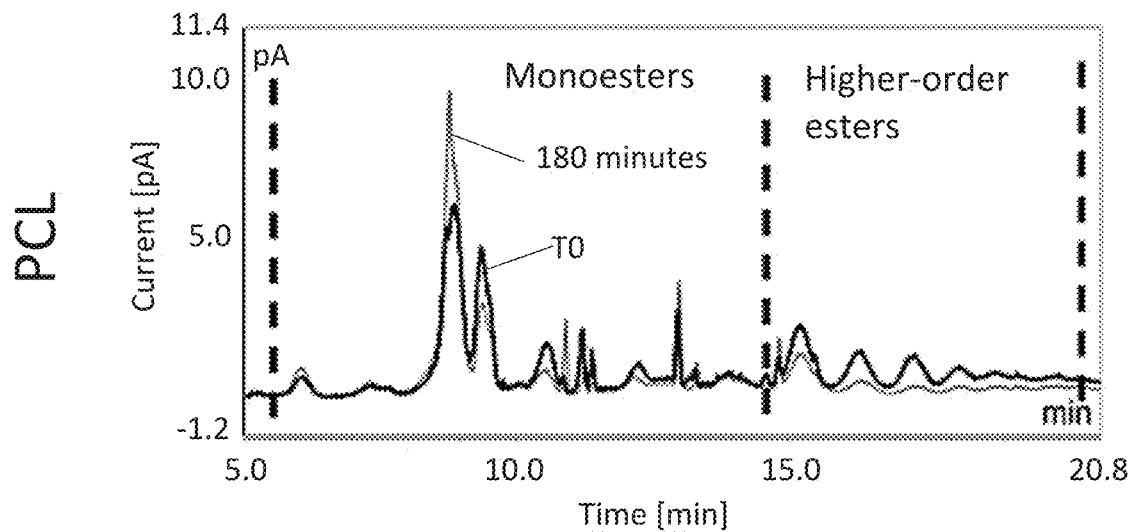
Figure 5A:
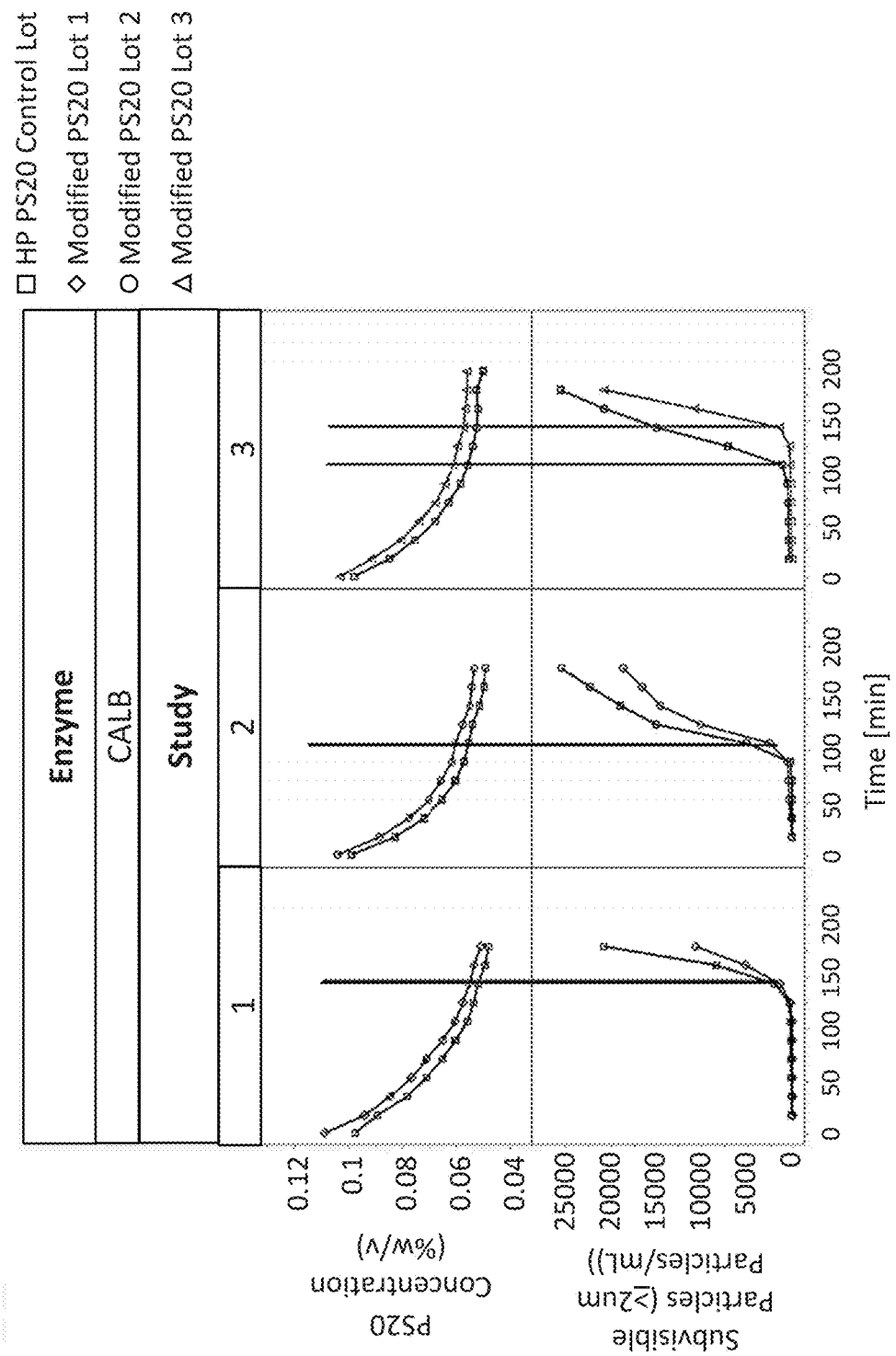
FIGS. 5A-B show PS20 degradation by non-immobilized enzymes in a histidine acetate buffer containing enzymes. PS20 concentration (% w/v) were determined by mixed-mode HPLC ELSD, and subvisible (≥2 µm) particle counts were determined by light obscuration.
Figure 5B:
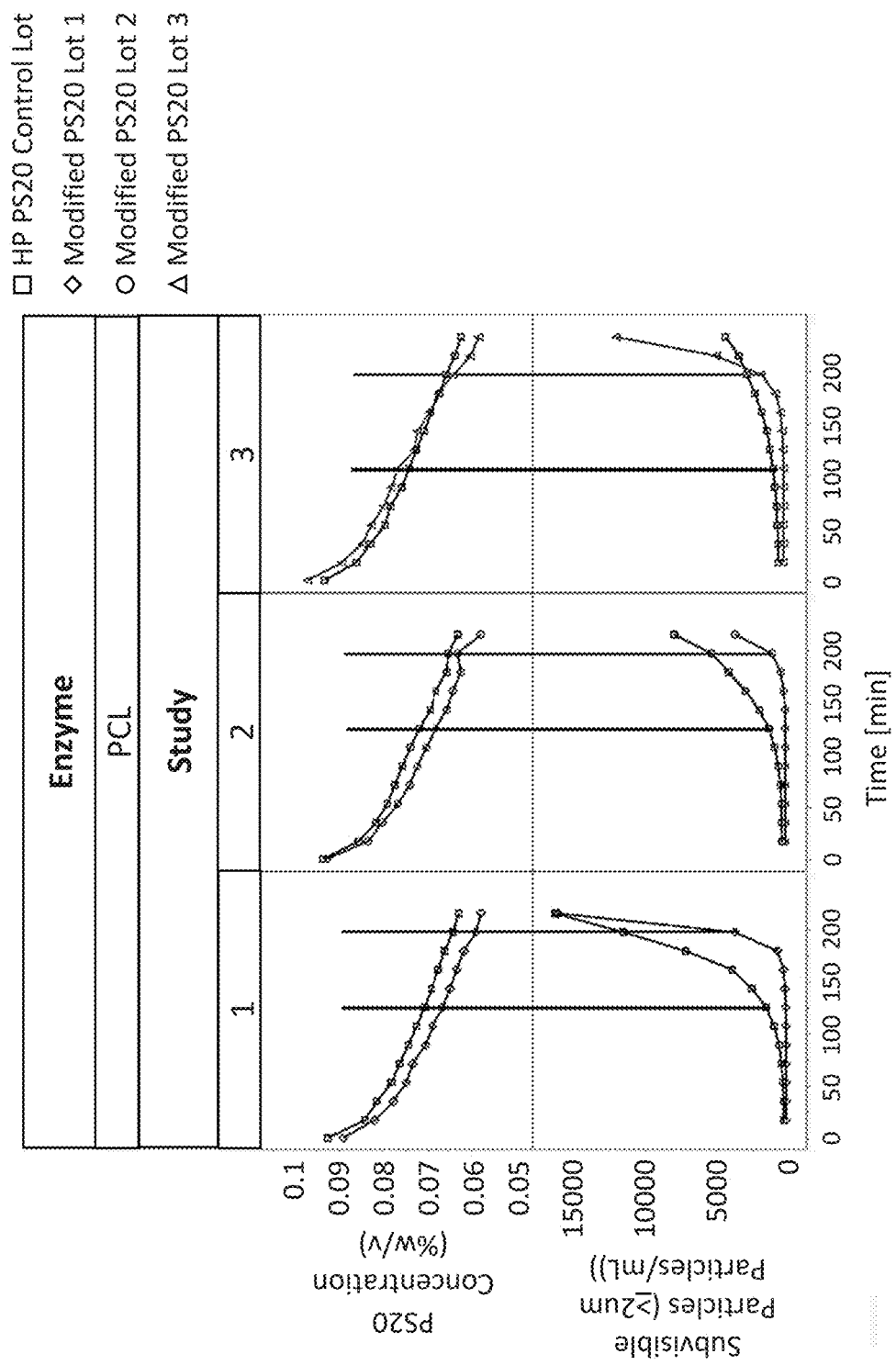
Figure 6:
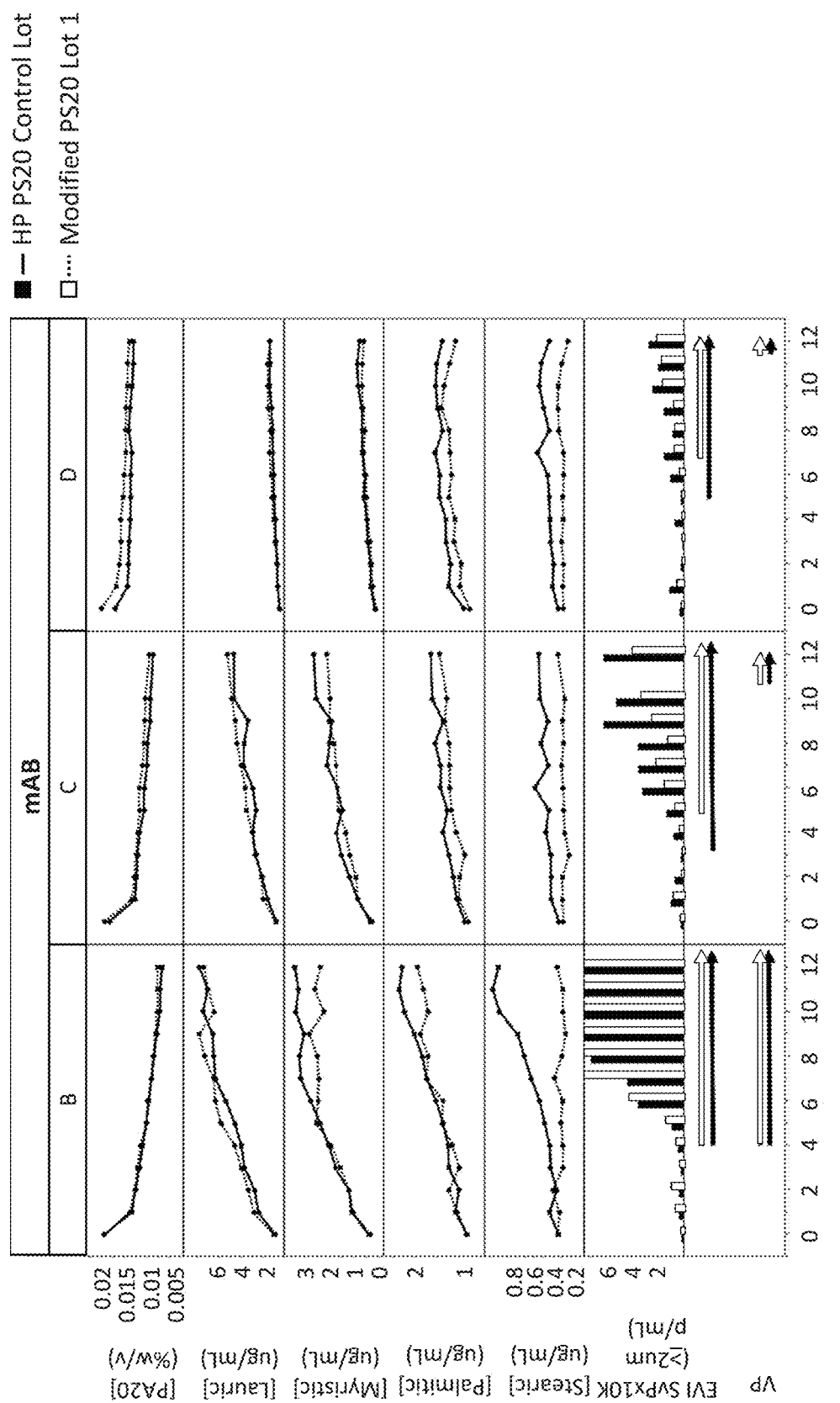
FIG. 6 shows a real-time 5° C. stability study comparing FFA particle formation of Modified HP PS20 and HP PS20 in fast degrading drug product formulations of mAb-B, C and D. PS20 concentration over time was measured by mixed-mode HPLC ELSD. Stearic, palmitic and myristic acid generation was measured by reversed phase MS. Subvisible (≥2 µm) particle measurements were performed by flow imaging microscopy. Both visual inspection and enhanced visual inspection were performed every week. The presence of visible particles is indicated by the arrows. VP=visible particles by visual inspection under a black and white background; EVI=enhanced visual inspection.
Figure 7A:
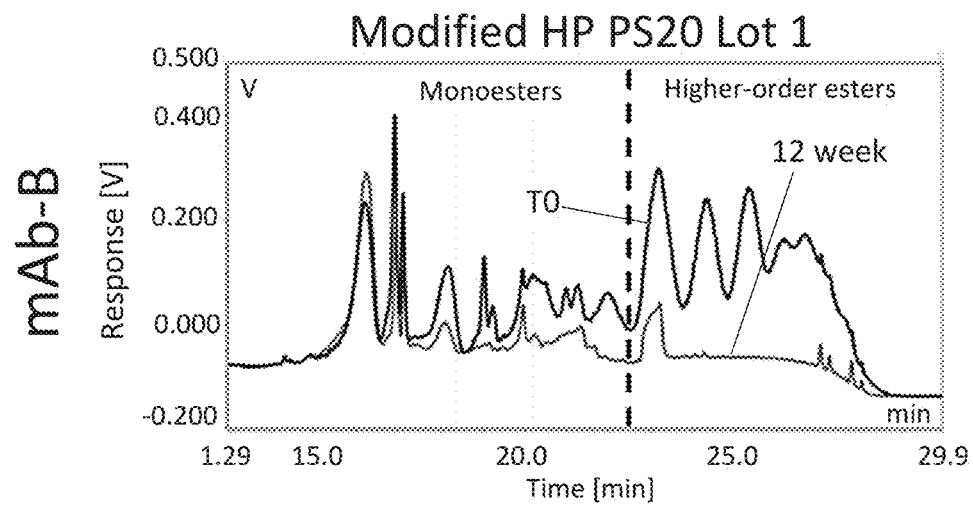
FIGS. 7A-F show reversed phase UHPLC measurements of the ester distribution at the beginning (T0) and end (12 week) of a real-time 5° C. stability study using fast degrading DP formulations of mAb-B, C and D to degrade PS20 from Modified HP PS20 lot 1 and on control lot HP PS20.
Figure 7B:
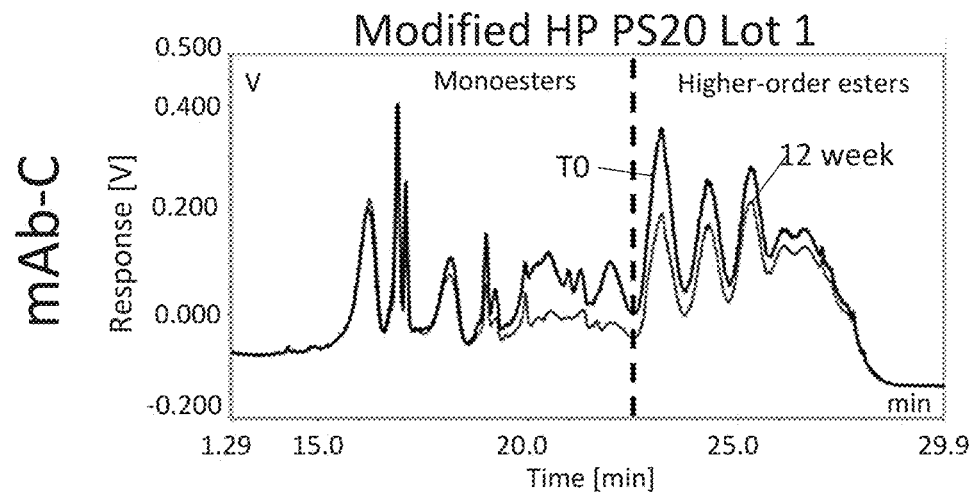
Figure 7C:
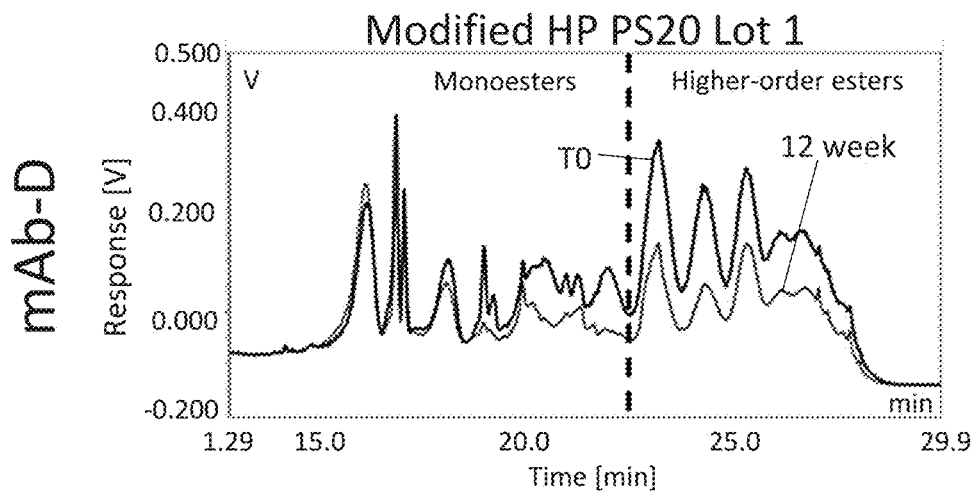
Figure 7D:
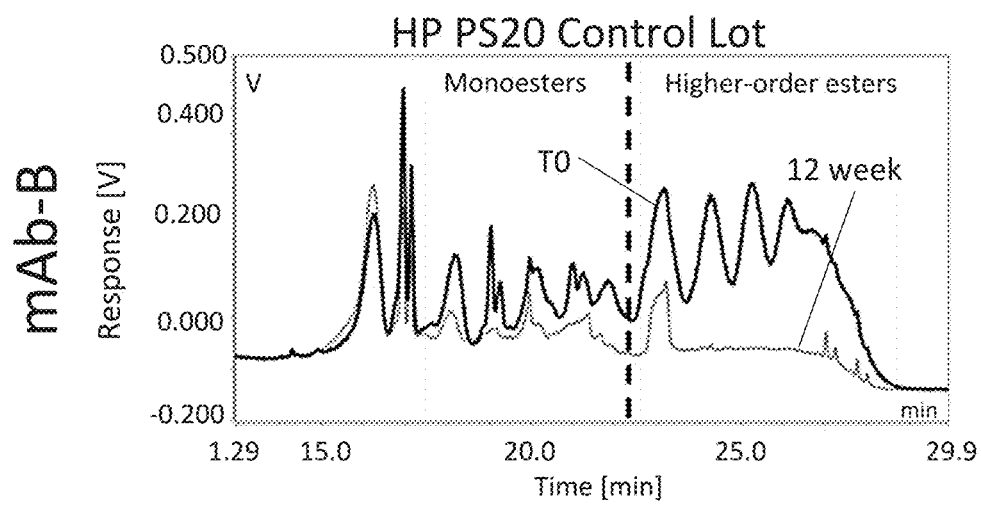
Figure 7E:
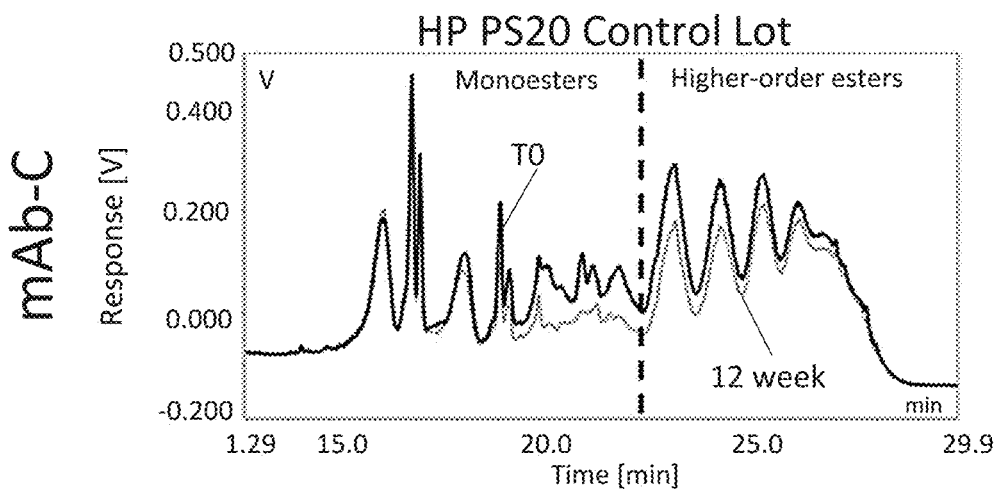
Figure 7F:
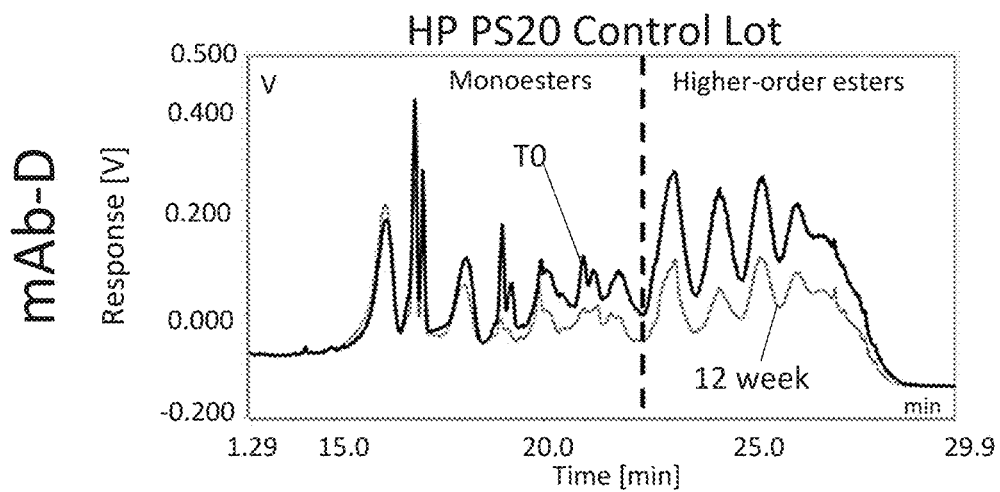
Figure 8C:
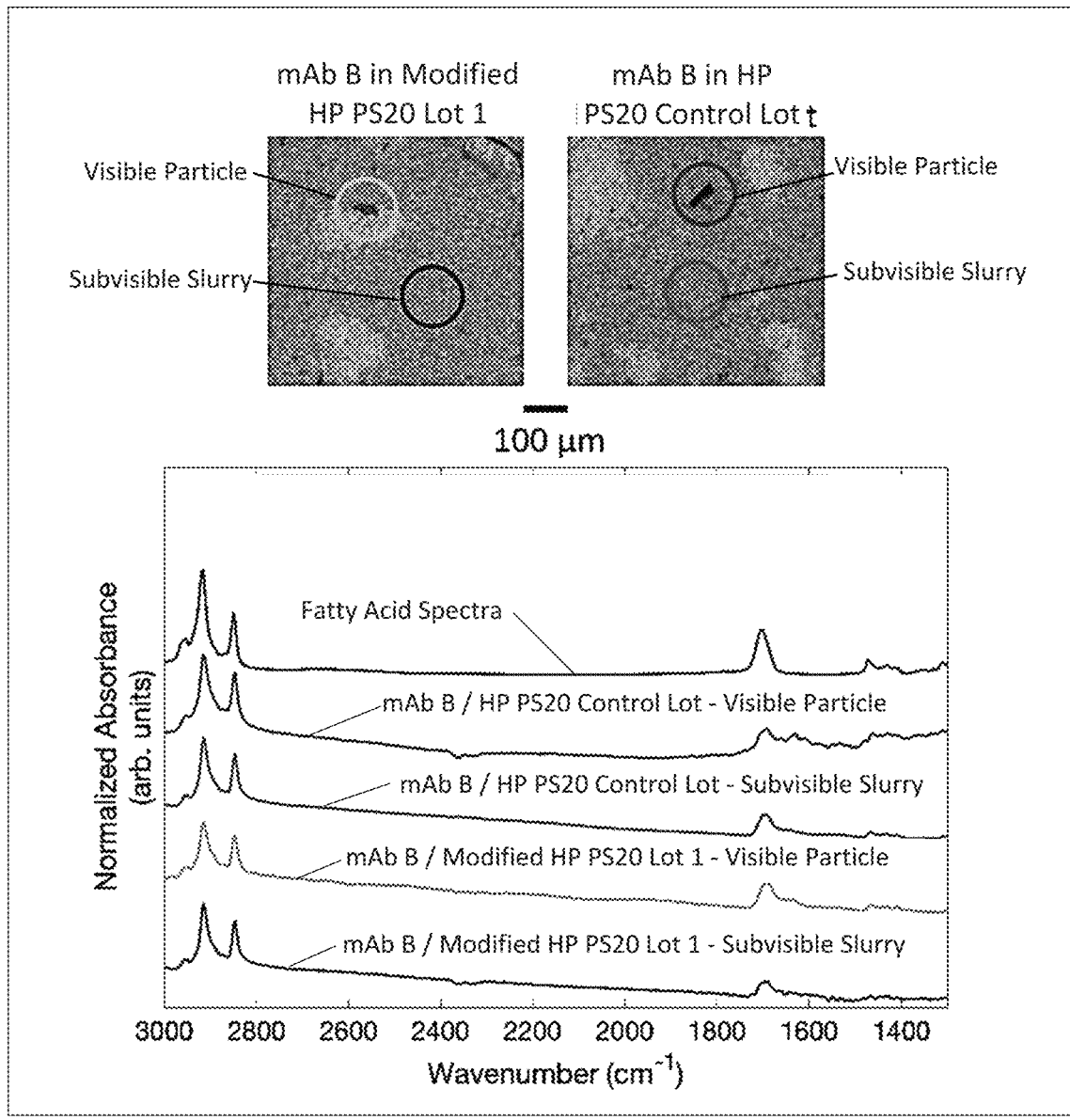
Figure 9:
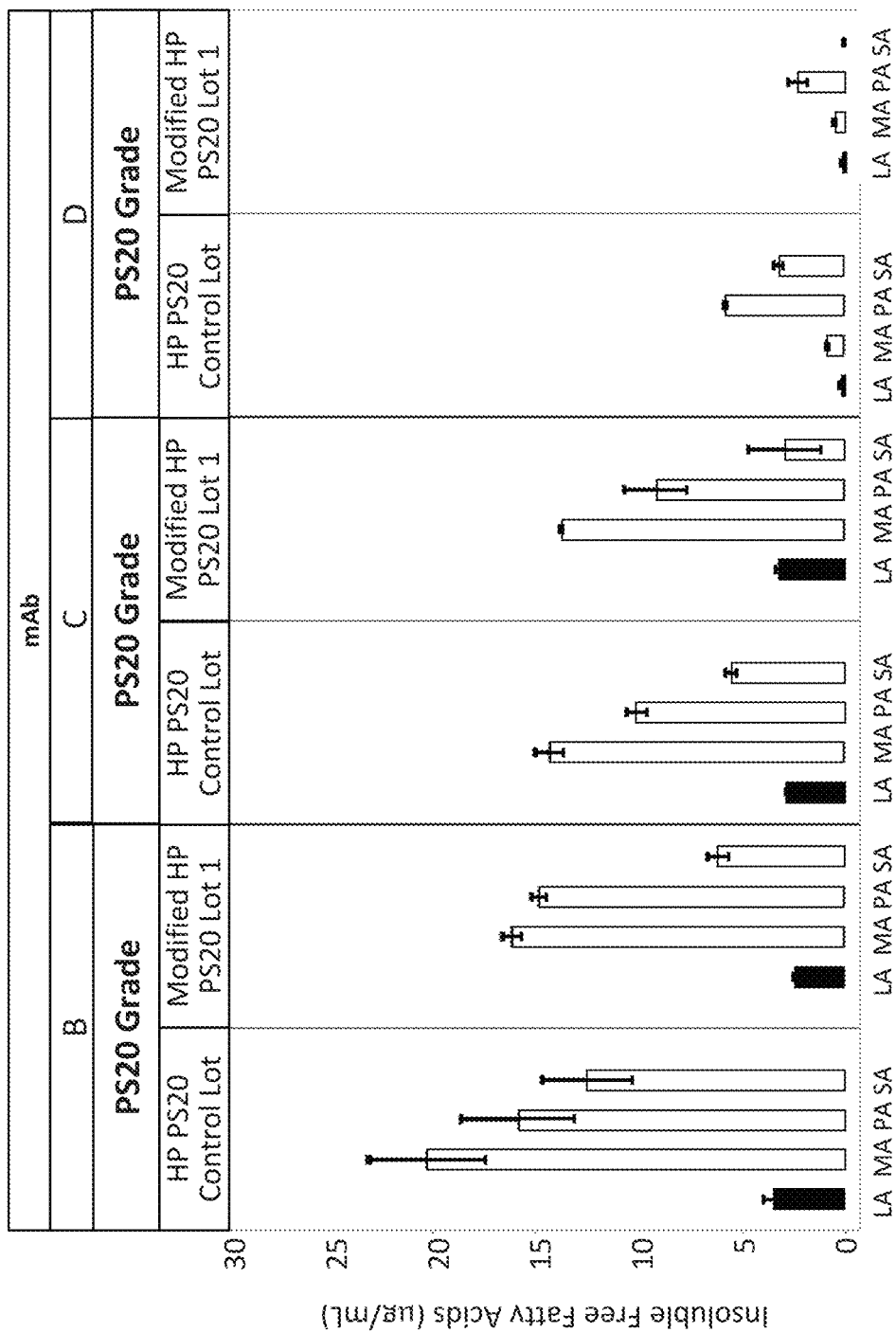
FIG. 9 shows the free fatty acid (FFA) distribution in the particles (insoluble fraction) measured at the 14 week time point of the 5° C. drug product stability study comparing FFA particle formation between Modified HP PS20 and HP PS20. Samples were filtered, resuspended and analyzed by reversed-phase MS. Of the three formulations, mAb-D had the latest onset of FFA particles. Therefore, at 14 weeks, the FFA distribution of the particles in the mAb-D formulation is most representative of the initial FFA distribution at particle onset compared with the mAb-B and C formulations. FFA measurements were performed in duplicate and the range is indicated by the error bars.

Trace metal ions like aluminum ($Al^{3+}$) may interact with FFAs to form FFA metal complexes which can precipitate out of aqueous formulations below the solubility limit of the uncomplexed FFAs (13). The Al content was <60 ppb in 10% w/v PS20 for both polysorbates (FIG. 3B) which translates to <0.4 ppb Al in a typical DP formulation with a PS20 concentration of 0.02-0.06% w/v. Metal induced nucleation of FFAs has been previously shown to occur at levels greater than 10 ppb $Al^{3+}$ (13). Therefore, the trace amount of Al observed in both Modified HP PS20 and HP PS20 raw material is considered negligible and is unlikely to affect the FFA metal nucleation propensity of either PS20 grade. Trace amounts of transition metal ions like iron ($Fe^{3+}$), Copper ($Cu^{2+}$), Chromium ($Cr^{3+}$) and Nickle ($Ni^{2+}$) are known to catalyze autoxidation of polysorbates (14, 15, 16, 17). Some differences in Fe, Ni and Cr were observed between 10% w/v Modified HP PS20 and HP PS20 with no clear trends (FIG. 3B). For instance, Fe levels were highest in Modified HP PS20 lot 3 followed by HP PS20 control lot and then Modified HP PS20 lots 1 and 2. To understand the significance of these differences, the oxidation propensity of Modified HP PS20 was compared to HP PS20 in a 40° C. placebo stability study and a methionine surrogate (Dansyl-methionine) oxidation study (data not shown). The results from the oxidation studies demonstrate that Modified HP PS20 and HP PS20 have similar susceptibility to oxidative degradation indicating that the differences observed in trace Fe, Ni and Cr levels of the do not appear to influence susceptibility to oxidation.

Enzymatic PS20 Degradation and FFA Particle Formation

To evaluate how Modified HP PS20 compares with HP PS20 in terms of the risk of forming FFA particles in solution in the absence of external nucleation factors, two sets of experiments were performed where PS20 was hydrolyzed either by non-immobilized enzymes or in a drug product (DP) formulation with rapid PS20 degradation. Furthermore, an experiment evaluating FFA particle risk in the presence of metal nucleation factors was also conducted using pre-degraded PS20; in this study, both Modified HP PS20 and HP PS20 were degraded by immobilized enzymes.

PS20 Degradation using Non-Immobilized Enzymes

Commercially available non-immobilized carboxylic ester hydrolases *Candida antarctica* Lipase B (CALB) and poly(ε-caprolactone) (PCL) were used to artificially hydrolyze Modified HP PS20 and HP PS20. PS20 degradation and subvisible particles were then monitored in the hydrolyzed samples. Visible particles were not monitored in this study since their onset has been previously shown to occur either at the same time or after subvisible particle onset in similar study setups using HP PS20 (18, 11). CALB and PCL have different specificities for PS20 degradation, which enables them to be used as an efficient model systems to compare FFA particle formation between different polysorbates. CALB preferentially degrades monoesters whereas PCL targets higher order esters (HOEs) in both Modified HP PS20 and HP PS20 (FIG. 4) (11, 19).

CALB degraded the three lots of Modified HP PS20 and the HP PS20 control lot at a similar rate (FIG. 5A). When degraded by CALB, Modified HP PS20 and HP PS20 samples showed an abrupt increase of >1000 particles/mL in subvisible (≥2 μm) particles after ~40% degradation. In the PCL study, all three lots of Modified HP PS20 degraded slightly faster than HP PS20 (FIG. 5B). It is important to note that small differences in degradation rates are expected between Modified HP PS20 and HP PS20 due to varying enzyme specificity towards certain FAE chain lengths (21, 21). Similar variability in degradation rates already exists between different batches of HP PS20 since FAE specifications for Modified HP PS20 are a subset of the USP/EP/ChP specifications applied to HP PS20 (Table 1 and FIG. 1).

In spite of slightly faster degradation, subvisible (≥2 μm) particle onset was delayed in Modified HP PS20 compared with HP PS20. All three lots of Modified HP PS20 showed an abrupt increase of >1000 particles/mL in subvisible (≥2 μm) particles after ~40% degradation unlike HP PS20 where the subvisible (≥2 μm) particles increased earlier, after ~30% degradation. The same trend was observed for subvisible particles ≥5, 10 and 25 μm (data not shown) for the CALB and PCL studies as it was for ≥2 μm particle size.

The delay in subvisible particle onset for Modified HP PS20 compared with HP PS20 in the PCL study but not the CALB study indicates potentially higher stearate ester content in the HOEs relative to monoesters. Modified HP PS20 has a very low stearate ester content of close to 0% compared with the HP PS20 control lot which is at 6% (Table 1). Stearic acid therefore may be the root cause of the early onset of FFA particles in HP PS20 compared to Modified HP PS20 when HOEs are targeted. However, when monoesters are targeted, palmitic acid may be the root cause of particle onset for both polysorbates. The difference in palmitate esters between Modified HP PS20 and HP PS20 is <3%.

As previously demonstrated, HOE degrading DPs are at a substantially higher risk of FFA particle formation than monoester degrading DPs due to the diminished FFA solubilizing capacity of monoesters relative to HOEs (2). The results of the PCL study show that replacing HP PS20 with Modified HP PS20 is expected to have a substantial benefit in HOE degrading DPs by allowing at least 10% additional degradation prior to FFA particle onset. The advantage afforded by Modified HP PS20 is likely to be greater in comparison to a more particle prone lot of HP PS20 (e.g., a lot with concentrations of stearate, palmitate and myristate ester at the high end of the allowed pharmacopoeia specifications) than the one used in our studies.

PS20 Degradation in Drug Product

FFA particle formation was compared between Modified HP PS20 and HP PS20 using monoclonal antibody (mAb) drug product (DP) formulation batches (mAb-A, mAb-B, mAb-C, and mAb-D) with rapid degradation of PS20 at 5° C. The degradation rates were similar between Modified HP PS20 and HP PS20 for the mAbs studied. After 12 weeks at 5° C., both polysorbates degraded by approximately 60% in the mAb-B, 50% in the mAb-C and 30% in the mAb-D formulation (FIG. 6). The pattern of degradation was similar across the mAbs and two polysorbates; both monoesters and HOEs were targeted (FIG. 7). Stearic, palmitic and myristic acids were generated at a faster rate in HP PS20 compared with Modified HP PS20 in all three mAb formulations. In the mAb-A formulation, visible particle (by both visual inspection and enhanced visual inspection) and subvisible (≥2 μm) particle onset occurred at the 4 week time point for both polysorbates. The same trends were observed in the mAb-B study for Modified HP PS20 lots 2 and 3 (data not shown) as it was for lot 1. For mAbs-C and D, particles were observed by enhanced visual inspection in the Modified HP PS20 formulation two weeks after the respective HP PS20 formulation (FIG. 6). By visual inspection, visible particle onset occurred at the same time point for both polysorbates; 11 weeks for mAb-C and 12 weeks for mAb-D. Subvisible (≥2 μm) particles also had a similar onset but the counts were higher for HP PS20 compared with Modified HP PS20 in both the mAb-C and D formulations. The same trend was observed for subvisible particles ≥5, 10 and 25 μm (data not shown) as it was for ≥2 μm particle size in all of the formulations. Furthermore, the subvisible particle morphology was similar across the three mAbs and two polysorbates; characteristic FFA flake- and needle-shaped particles as described previously (20). The particles in the mAb-B, C and D formulations were filtered on a 0.8 μm gold polycarbonate filter at 14 weeks. Attempts to isolate particles resulted in a slurry with a few discrete particles all of which were identified as FFAs by FT-IR spectroscopy (FIG. 8A-C).

Overall, the results of the 5° C. DP stability study demonstrate a slight delay in FFA particles for the Modified HP PS20 grade compared with HP PS20 grade. The pattern of degradation for all 3 mAb formulations targeted both monoesters and HOEs. It was hypothesized that in this study, similar to the CALB study, palmitic acid is the root cause of the particle onset for both polysorbates. This hypothesis was confirmed by measuring the FFA content in the particles for the three mAb formulations at 14 weeks. Of the three formulations, mAb-D had the latest onset of FFA particles. Therefore, at 14 weeks, the FFA distribution of the particles in the mAb-D formulation is most representative of the initial FFA distribution at particle onset unlike the mAb-B and C formulations. The particles in the mAb-D formulation contained the highest proportion of palmitic acid relative to stearic, myristic or lauric acid for Modified HP PS20 and HP PS20 (FIG. 9) indicating that palmitic acid precipitated first. The particles (insoluble fraction) in the mAb-B and C formulations contained the highest proportion of myristic acid relative to the other long chain FFAs for both polysorbates. High myristic acid levels have been previously observed in aged FFA particles (20) as PS20 continues to degrade but not in early onset particles. Therefore, a high myristate content in the particles of the mAb-B and C formulations further indicates that they have aged and are not representative of early onset particles. Interestingly, stearic acid was present in the particles of the Modified HP PS20 mAb-B formulation, albeit at lower levels than the HP PS20 formulation. This indicates that although the CoA shows 0% stearate ester content, there still might be some stearate esters present in Modified HP PS20. However, stearic acid is unlikely to be the triggering factor for particles in Modified HP PS20 as demonstrated by the FFA distribution of the particles in the mAb-D formulation.

The propensity to form FFA particles upon hydrolytic degradation was lower in Modified HP PS20 compared with standard PS20. The benefit was more pronounced when the pattern of PS20 degradation was specifically targeted towards HOEs. Replacing HP PS20 with Modified HP PS20 in HOE degrading DPs may allow for at least 10% additional degradation prior to FFA particle onset. Furthermore, Modified HP PS20 demonstrated a lower propensity to nucleate and form FFA metal salts upon degradation compared with standard PS20. The advantage afforded by Modified HP PS20 is likely to be even greater in comparison to a more particle prone lot of HP PS20 (manufactured at the high end of stearate, palmitate and myristate esters) than the one used in our studies. Overall, the data show that the presence of long chain FAEs in PS20 renders it more susceptible to forming FFA particles upon degradation. Tighter control on the FAE levels in the PS20 raw material may enhance other mitigation efforts against PS20 degradation by lowering the occurrence and improving the consistency of FFA particle formation.

Metal Nucleation of Free Fatty Acids

FFA solubility is reduced in the presence of external nucleation factors such as $NaAlO_2$ and $CaCl_2$) leaching from DP glass vials (13). Negatively charged FFAs can interact with multivalent cations, such as $Al^{3+}$ and form insoluble FFA complexes which precipitate in aqueous solutions at concentrations well below the aqueous solubility limits of the uncomplexed FFAs (13). An increase in FFA chain length is expected to accelerate the onset of visible FFA metal salts which suggests that Modified HP PS20 may be at a lower risk of FFA metal nucleation compared with HP PS20 (13). The propensity of Modified HP PS20 and HP PS20 to form metal FFA complexes was compared by spiking in 10% degraded PS20 into aqueous buffer solutions containing 0-250 ppb $Al^{3+}$. Both Modified HP PS20 and HP PS20 were degraded using immobilized enzymes MML which targets HOEs and CAL which degrades both monoesters and HOEs (10). The nominal PS20 concentration in the spiked solutions was 0.04% w/v. The samples were subsequently placed at 5° C. and monitored for visible and subvisible particle formation.

For the CAL study, an earlier onset of visible particles was observed as the $Al^{3+}$ levels were increased for HP PS20 (Table 2). The three lots of Modified HP PS20 showed a delayed visible particle onset and fewer particles per container compared with HP PS20 at all $Al^{3+}$ levels. Moreover, for Modified HP PS20, visible particles were only observed in samples containing 100 ppb $Al^+$ but not in the 50 or 250 ppb $Al^+$ samples. These results indicate that the long chain FFAs such as myristic, palmitic and stearic acids play a role in the early nucleation of FFAs observed in HP PS20. Modified HP PS20 is expected to have lower levels of long chain FFAs after 10% enzymatic degradation compared with HP PS20. Consequently, 50 ppb of $Al^{3+}$ may be insufficient to generate enough fully complexed FFAs to coalesce and trigger particle growth to a visible size in Modified HP PS20. In contrast, the 250 ppb $Al^+$ samples may have too many nucleation sites and therefore a relatively higher number of partially complexed (FFA:Al ratio of 1:1 or 2:1) FFAs which are less likely to coalesce into visible particles than fully complexed 3:1 FFA:Al salts.

TABLE 2

Visible particles in PS20 pre-degraded by enzyme CAL and spiked with $Al^{3+}$

| PS Grade | Degradation | Aluminum conc. (ppb) | Visible Particles d2 | d6 | d13 | d15 | d21 |
|---|---|---|---|---|---|---|---|
| HP PS20 Control Lot | 0% 10% (CAL) | 0 0 50 100 250 | / / / / xxx | / / / xx xxx | / / xxx xxx xxx | / / xx xxx xxx | / / xx xxx xxx |
| RO HP PS20 Lot 1 | 0% 10% (CAL) | 0 0 50 100 250 | / / / / / | / / / / / | / / / / / | / / / / / | / / / xx / |
| RO HP PS20 Lot 2 | 0% 10% (CAL) | 0 0 50 100 250 | / / / / / | / / / xx / | / / / xx / | / / / xx / | xx / / xxx / |
| RO HP PS20 Lot 3 | 0% 10% (CAL) | 0 0 50 100 250 | / / / / / | / / / / / | / / / xxx / | / / / xxx / | / / / xx / |

/ = 0-4 visible particles, xx = 4-7 particles, xxx = >7 particles per container (20 mL). Results are reported as the average number of particles in 3 containers.

For the MML study, an earlier onset of visible particles was observed with increasing $Al^{3+}$ levels for HP PS20, similar to the CAL study (Table 3). Lots 1 and 2 of Modified HP PS20 had similar particle onset as HP PS20 in the 50 and 100 ppb containing samples. Visible particles were not observed in the 250 ppb $Al^{3+}$ arm for Modified HP PS20 lots 1 and 2 likely due to too many nucleation sites and partial complexation. Modified HP PS20 lot 3 contained visible particles in the control without Al which were identified as protein contamination by FT-IR. Therefore, this sample subset was excluded from the study.

TABLE 3

Visible particles in PS20 pre-degraded by enzyme MML and spiked with $Al^{3+}$

| PS Grade | Degradation | Aluminum conc. (ppb) | Visible Particles (Ph. Eur.) d2 | d6 | d13 | d15 | d21 |
|---|---|---|---|---|---|---|---|
| HP PS20 Control Lot | 0% 10% (MML) | 0 0 50 100 250 | / / / / xxx | / / / / xxx | / / / xxx xxx | / / xxx xxx xxx | / / xxx xxx xxx |
| RO HP PS20 Lot 1 | 0% 10% (MML) | 0 0 50 100 250 | / / / / / | / / / / / | / / xx xxx / | / / xxx xxx / | / / xxx xxx / |
| RO HP PS20 Lot 2 | 0% 10% (MML) | 0 0 50 100 250 | / / / / / | / / / / / | / / / xx / | / / xx xxx / | xx / xxx xx / |

/ = 0-4 visible particles, xx = 4-7 particles, xxx = >7 particles per container (20 mL). Results are reported as the average number of particles in 3 containers. Results are reported as the average number of particles in 3 containers. Modified HP PS20 Lot 3 degraded by MML contained visible particles in the control lot without $Al^{3+}$ which was confirmed as protein contamination by FT-IR and therefore, not included Similar onset of visible particles between HP PS20 and Modified HP PS20 in the MML study, at 50 and 100 ppb $Al^{3+}$, may be attributable to a higher FFA concentration in the 10% degraded PS20 solution by MML relative to CAL.

MML primarily degrades HOEs (diesters and triesters) unlike CAL which degrades both monoesters and HOEs. Therefore, MML is likely to generate a stoichiometrically higher amount of FFAs per microgram of degraded PS20. The FFA concentration in the MML samples of both the HP PS20 and Modified HP PS20 may be too high to resolve the differences between their nucleation propensity at 50 and 100 ppb $Al^{3+}$.

Cumulative subvisible (≥2 μm) particle counts by light obscuration after 21 days at 5° C. were higher in the 250 ppb $Al^{3+}$ containing HP PS20 samples compared with Modified HP PS20 for both enzymes (Tables 2 and 3). The 50 and 100 ppb $Al^+$ samples had similar subvisible particle counts between the two polysorbates. These results provide supporting evidence of the delayed onset of FFA metal salt particles in Modified HP PS20 compared with HP PS20. However, the differences observed between the polysorbates are considered insignificant given that the subvisible (≥2 μm) particle counts were <1000 particles/mL for all samples. Overall, the results suggest that the risk of metal nucleation of FFAs upon PS20 degradation and the subsequent formation of visible particles is reduced in Modified HP PS20 compared with HP PS20.

Functional Characterization

Modified HP PS20 grades reduce FFA particle formation upon degradation as shown in the examples above. In addition, the Modified HP PS20 grades showed no material loss of functionality compared to HP PS20. For example, the oxidation propensity of Modified HP PS20 and HP PS20 was comparable both in terms of PS20 oxidative degradation and methionine oxidation. A methionine concentration of 10 mM was able to mitigate oxidative degradation of both PS20 grades. In addition, agitation studies in vials and in i.v. bags showed that the Modified HP PS20 grade containing lower levels and better control of long chain FAEs demonstrated equivalent functionality compared with HP PS20 in protecting mAbs from air-liquid interfacial stresses.

CONCLUSION

The Modified HP PS20 has a lower propensity to form FFA particles compared with HP PS20, likely due to the more soluble composition of FFAs. The benefit was more pronounced when the pattern of PS20 degradation was specifically targeted towards HOEs. In a formulation comprising an HOE degrading drug product, the Modified HP PS20 may allow for at least 10% additional degradation compared to HP PS20 prior to FFA particle onset, resulting in delayed FFA particle formation. Furthermore, Modified HP PS20 demonstrated a delayed onset of FFA metal salts upon hydrolytic degradation compared with HP PS20. The data overall suggest that Modified HP PS20 is a more fit for purpose surfactant compared with HP PS20 for biopharmaceutical drug products by reducing FFA particle formation risks while still maintaining overall drug product stability.

REFERENCES

1. Hewitt D, Alvarez M, Robinson K, Ji J, Wang Y J, Kao Y-H, et al. Mixed-mode and reversed-phase liquid chromatography-tandem mass spectrometry methodologies to study composition and base hydrolysis of polysorbate 20 and 80. Journal of Chromatography A. 2011; 1218(15):2138-45.
2. Doshi N, Martin J, Tomlinson A. Improving Prediction of Free Fatty Acid Particle Formation in Biopharmaceutical Drug Products: Incorporating Ester Distribution during Polysorbate 20 Degradation. Mol Pharm. 2020; 17(11):4354-63
3. Li Y, Hewitt D, Lentz Y K, Ji J A, Zhang T Y, Zhang K. Characterization and stability study of polysorbate 20 in therapeutic monoclonal antibody formulation by multidimensional ultrahigh-performance liquid chromatography-charged aerosol detection-mass spectrometry. Analytical chemistry. 2014; 86(10):5150-7.
4. Zhang S, Xiao H, Molden R, Qiu H, Li N. Rapid polysorbate 80 degradation by liver carboxylesterase in a monoclonal antibody formulated drug substance at early stage development. Journal of Pharmaceutical Sciences. 2020; 109(11):3300-7.
5. Honemann M N, Wendler J, Graf T, Bathke A, Bell C H. Monitoring polysorbate hydrolysis in biopharmaceuticals using a QC-ready free fatty acid quantification method. Journal of Chromatography B. 2019; 1116:1-8.
6. Siska C C, Pierini C J, Lau H R, Latypov R F, Fesinmeyer R M, Litowski J R. Free fatty acid particles in protein formulations, part 2: contribution of polysorbate raw material. J Pharm Sci. 2015; 104(2):447-56.
7. Werk T, Volkin D B, Mahler H-C. Effect of solution properties on the counting and sizing of subvisible particle standards as measured by light obscuration and digital imaging methods. European Journal of Pharmaceutical Sciences. 2014; 53:95-108.
8. USP, (790) Visible Particulates in Injections, The United States Pharmacopoeia—National Formulary, USP 29-NF, 2016.
9. Ph. Eur., General, particulate contamination: visible particles, in: The European Pharmacopoeia, seventh ed., 2008 (Chapter 2.9.20).
10. Graf T, Abstiens K, Wedekind F, Elger C, Markus H, Wurth C, et al. Controlled Polysorbate 20 Hydrolysis—A new Approach to Assess the Impact of Polysorbate 20 Degradation on Biopharmaceutical Product Quality in Shortened Time. European Journal of Pharmaceutics and Biopharmaceutics. 2020.
11. Doshi N, Fish R, Padilla K, Yadav S. Evaluation of Super Refined™ Polysorbate 20 With Respect to Polysorbate Degradation, Particle Formation and Protein Stability. Journal of Pharmaceutical Sciences. 2020; 109(10):2986-95.
12. Fish R, Lin J, Doshi N. Impact of Silicone Oil on Free Fatty Acid Particle Formation due to Polysorbate 20 Degradation. Pharmaceutical Research. 2020; 37(11):1-15.
13. Allmendinger A, Lebouc V, Bonati L, Woehr A, Kishore R S, Abstiens K. Glass leachables as a nucleation factor for free fatty acid particle formation in biopharmaceutical formulations. Journal of Pharmaceutical Sciences. 2021; 110(2):785-95.
14. Kerwin B A. Polysorbates 20 and 80 used in the formulation of protein biotherapeutics: structure and degradation pathways. J Pharm Sci. 2008; 97(8):2924-35.
15. Dwivedi M, Blech M, Presser I, Garidel P. Polysorbate degradation in biotherapeutic formulations: identification and discussion of current root causes. International journal of pharmaceutics. 2018; 552(1-2):422-36.
16. Gopalrathnam G, Sharma A N, Dodd S W, Huang L. Impact of stainless steel exposure on the oxidation of polysorbate 80 in histidine placebo and active monoclonal antibody formulation. PDA journal of pharmaceutical science and technology. 2018; 72(2):163-75.

17. Ha E, Wang W, Wang Y J. Peroxide formation in polysorbate 80 and protein stability. J Pharm Sci. 2002; 91(10):2252-64.
18. Doshi N, Giddings J, Luis L, Wu A, Ritchie K, Liu W, Chan W, Taing R, Chu J, Sreedhara Kannan A. A Comprehensive Assessment of All-Oleate Polysorbate 80: Free Fatty Acid Particle Formation, Interfacial Protection and Oxidative Degradation. Pharmaceutical Research. 2021:1-8
19. McShan A C, Kei P, Ji J A, Kim D C, Wang Y J. Hydrolysis of Polysorbate 20 and 80 by a Range of Carboxylester Hydrolases. PDA J Pharm Sci Technol. 2016; 70(4):332-45.
20. Saggu M, Demeule B, Jiang L, Kammerer D, Nayak P K, Tai M, Xiao N, Tomlinson A. Extended Characterization and Impact of Visible Fatty Acid Particles-A Case Study With a mAb Product. Journal of Pharmaceutical Sciences. 2021; 110(3):1093-102.
21. Benito-Gallo P, Franceschetto A, Wong J C, Marlow M, Zann V, Scholes P, et al. Chain length affects pancreatic lipase activity and the extent and pH-time profile of triglyceride lipolysis. European journal of pharmaceutics and biopharmaceutics. 2015; 93:353-62.
22. Shinomiya M, McLean L, Jackson R L. Chain length dependence of phosphatidylcholine hydrolysis catalyzed by lipoprotein lipase. Effect of apolipoprotein C-II. Journal of Biological Chemistry. 1983; 258(23): 14178-80.

Example 2. Improving Prediction of Free Fatty Acid Particle Formation in Biopharmaceutical Drug Products: Incorporating Ester Distribution During Polysorbate 20 Degradation Fatty acid esters in PS20 can form free fatty acids (FFA), which, in turn, may result in formation of visible or subvisible particles in PS20-containing formulations. Higher order esters may facilitate dissolution of FFAs in formulations comprising PS20. Degradation products of PS20 may include mono-esters resulting from the degradation of HOEs; for example, the degradation of a di-ester could result in a mono-ester if one of the fatty acid esters is cleaved. Therefore, PS20 degradation may change the ester distribution of the PS20 remaining in solution after degradation compared to the starting raw material.

The present disclosure also provides a model, for example, for formulations comprising PS20, which takes into account pH and PS20 concentration, as well as PS20 ester distribution and their effects on FFA solubility. The model predicts that increasing the pH of a formulation above the pKa of a specific FFA increases its solubility exponentially due to the ionized form of the FFA being significantly more soluble than the non-ionized form. The model also predicts that FFA solubility increases with increasing PS20 concentration. The model also incorporates the contribution of the changing ester distribution with enzymatic degradation as an additional factor for improved accuracy.

To create the model, first, FFA solubility was measured at different formulation pH's at a constant PS20 concentration. The relationship was fit to a modified form of the Henderson-Hasselbalch equation to experimentally determine the pKa of each of lauric, myristic and palmitic acid and the solubility of the non-ionized FFA. FFA solubility increases with increasing pH as it approaches and surpasses the pKa of the respective FFA. The pH dependence was attributed to the higher fraction of ionized FFA (significantly more soluble than the non-ionized fraction) in solutions at higher pH. Second, FFA solubility was measured at different PS20 concentrations at a constant pH. This data was fit to an empirically derived function. Lastly, the individual equations describing FFA solubility as a function of pH and PS20 concentration were combined into one semi-empirical relationship summarized in Equation 1:

$$FFA \text{ Solubility} = (\beta_1 + \beta_1 \times \frac{pH}{10^{pH-\beta_2}}) * \frac{PS20 \text{ Term}}{(2443.5[PS20]^2 + 150.0[PS20] + 5.0)}{14.8} \qquad (Eq.\ 1)$$

where $\beta_1$ is the solubility of the non-ionized fatty acid and $\beta_2$ is the experimentally determined pKa. Values for $\beta_1$ and $\beta_2$ for lauric, myristic and palmitic acid are listed in Table 4.

TABLE 4

Constants for Lauric, Myristic, and Palmitic Acids in the 'pH term' of the FFA solubility model (Equation 1)

| | Lauric (C12) Acid | Myristic (C14) Acid | Palmitic (C16) Acid |
|---|---|---|---|
| Solubility of the non-ionized FFA ($\beta_1$) | 9.97 | 3.87 | 1.35 |
| Experimentally determined pKa ($\beta_2$) | 5.71 | 6.67 | 7.01 |

To further update the model, we generated "mock-degraded" PS20 (MD PS20) by fractionating PS20 into mono-esters and HOEs and mixing them in different mass ratios. The MD PS20s span a range of % HOE mass fractions to mimic potential ester distributions of hydrolytically degraded PS20. FFA solubility was measured at different concentrations of the MD PS20 solutions to generate a more accurate model of FFA solubility and subsequent particle risk. Second, in an update to the solubility model, the "PS20 term" of equation 1 was modified to include PS20 ester distribution, in addition to total PS20 content, as a third variable impacting FFA solubility. It was found that as PS20 concentration decreased, FFA solubility also decreased. Combining the pH term from Equation 1 with Equation 2 allows the estimation of FFA solubility at any combination of pH, PS20 concentration and HOE peak area fraction. Equation 2 is as follows:

$$\text{Lauric Acid Solubility} = 289.5*[PS20] - 12.7*HOE + ([PS20] - 0.04)*((HOE - 0.5)*306.8) - 4.1 \qquad (Eq.\ 2)$$

where HOE is the higher order ester to total peak area fraction of PS20.

To bridge equations 1 and 2, a factor R was first calculated using Equation 2. R is defined by Equation 3a as the ratio of FFA solubility at the desired PS20 concentration and HOE peak area fraction (numerator) to the FFA solubility at 0.04% (w/v) PS20 and HOE peak area fraction of 0.41 (denominator). Equations 3a and 3b are as follows:

$$R = \frac{289.5*[PS20] - 12.7*HOE + ([PS20] - 0.04)*((HOE - 0.5)*306.8) - 4.1}{289.5*0.04 - 12.7*0.41 + (0.04 - 0.04)*((0.41 - 0.5)*306.8) - 4.1} \qquad (Eq.\ 3a)$$

which is simplified to $$R = \frac{289.5*[PS20] - 12.7*HOE + ([PS20] - 0.04)*((HOE - 0.5)*306.8) - 4.1}{12.8} \quad \text{(Eq. 3b)}$$

R is expected to be independent of pH and can be multiplied by the pH term of Equation 1 to yield the final expression of FFA solubility for the refined model, described by Equation 4. Equation 4 is as follows:

$$FFA \text{ Solubility} = (\beta_1 + \beta_1 \times 10^{pH-\beta_2}) \times \quad \text{(Eq. 4)}$$
$$\frac{289.5*[PS20] - 12.7*HOE + ([PS20] - 0.04)*((HOE - 0.5)*306.8) - 4.1}{12.8}$$

where $\beta_1$ is the solubility of the non-ionized fatty acid and $\beta_2$ is the experimentally determined pKa and HOE is the higher order ester to total peak area fraction of PS20.

This semi-empirical relationship presented in Equation 4 can be utilized to predict the solubility of lauric, myristic, and palmitic acid in a given formulation buffer at 5° C. based on its pH, PS20 concentration and HOE peak area fraction. One assumption for the model is that the solubilities of myristic and palmitic acids change in the same manner as that of lauric acid as a function of PS20 concentration and HOE peak area fraction. We previously verified this assumption by comparing measured and predicted FFA solubilities at different pH and PS20 concentrations and is expected to hold true in the new model[36].

The final model helps explain why formulations with similar pH and PS20 degradation rates may have very different propensities for particle formation depending on specificity of degradation towards either mono- or HOEs of PS20. It also suggests that formulations that degrade HOEs, especially those formulated at low pH, are at highest risk of FFA particle formation due hydrolytic PS20 degradation.

To utilize the model as a tool for particle prediction in biopharmaceutical drug products over shelf-life, the following measurements are recommended at 5° C. stability time points 1) formulation pH 2) total PS20 concentration (using mixed-mode HPLC ELSD) and 3) HOE peak area fraction (using shallow gradient UHPLC CAD). These measurements will enable the use of the model to predict solubility limits of lauric, myristic and palmitic acid solubility at each stability time point. Comparing FFA solubility limits to measured FFA amounts over time and extrapolating to find the intersection point can help predict when FFA are expected to precipitate and form visible or sub-visible particles.

ADDITIONAL REFERENCES

23. Bam N B, Cleland J L, Yang J, Manning M C, Carpenter J F, Kelley R F, et al. Tween protects recombinant human growth hormone against agitation-induced damage via hydrophobic interactions. J Pharm Sci. 1998; 87(12):1554-9.
24. Mahler H C, Printz M, Kopf R, Schuller R, Muller R. Behaviour of polysorbate 20 during dialysis, concentration and filtration using membrane separation techniques. J Pharm Sci. 2008; 97(2):764-74.
25. Mahler H-C, Huber F, Kishore R S, Reindl J, Rückert P, Milner R. Adsorption behavior of a surfactant and a monoclonal antibody to sterilizing-grade filters. Journal of pharmaceutical sciences. 2010; 99(6):2620-7.
26. Tomlinson A, Zarraga I E, Demeule B. Characterization of Polysorbate Ester Fractions and Implications on Protein Drug Product Stability. Molecular Pharmaceutics. 2020.
27. Pharmaceutical and Medical Devices Agency. Japanese Pharmacopoeia. 17th ed. Tokyo: Pharmaceutical and Medical Devices Agency; 2017.
28. United States Pharmacopeial Convention. United States Pharmacopeia and National Formulary. Rockville, MD: United States Pharmacopeial Convention; 2018.
29. Council of Europe. European Pharmacopoeia. 9.3rd ed. Strasbourg, France: European Medicines Agency; 2017.
30. Cumme G A, Blume E, Bublitz R, Hoppe H, Horn A. Composition analysis of detergents of the polyoxyethylene type: comparison of thin-layer chromatography, reversed-phase chromatography and matrix-assisted laser desorption/ionization mass spectrometry. Journal of Chromatography A. 1997; 791(1-2):245-53.
31. Zhang L, Yadav S, Demeule B, Wang Y J, Mozziconacci O, Schneich C. Degradation Mechanisms of Polysorbate 20 Differentiated by (18) O-labeling and Mass Spectrometry. Pharm Res. 2017; 34(1):84-100.
32. Chiu J, Valente K N, Levy N E, Min L, Lenhoff A M, Lee K H. Knockout of a difficult-to-remove CHO host cell protein, lipoprotein lipase, for improved polysorbate stability in monoclonal antibody formulations. Biotechnol Bioeng. 2017; 114(5):1006-15.
33. Dixit N, Salamat-Miller N, Salinas P A, Taylor K D, Basu S K. Residual Host Cell Protein Promotes Polysorbate 20 Degradation in a Sulfatase Drug Product Leading to Free Fatty Acid Particles. J Pharm Sci. 2016; 105(5):1657-66.
34. Kranz W, Wuchner K, Corradini E, Berger M, Hawe A. Factors Influencing Polysorbate's Sensitivity Against Enzymatic Hydrolysis and Oxidative Degradation. J Pharm Sci. 2019; 108(6):2022-32.
35. Labrenz S R. Ester hydrolysis of polysorbate 80 in mAb drug product: evidence in support of the hypothesized risk after the observation of visible particulate in mAb formulations. J Pharm Sci. 2014; 103(8):2268-77.
36. Doshi N, Demeule B, Yadav S. Understanding Particle Formation: Solubility of Free Fatty Acids as Polysorbate 20 Degradation Byproducts in Therapeutic Monoclonal Antibody Formulations. Mol Pharm. 2015; 12(11):3792-804.
37. Tomlinson A, Demeule B I, Lin B, Yadav S. Polysorbate 20 degradation in biopharmaceutical formulations: quantification of free fatty acids, characterization of particulates, and insights into the degradation mechanism. Molecular pharmaceutics. 2015; 12(11):3805-15.
38. Saggu M, Liu J, Patel A. Identification of Subvisible Particles in Biopharmaceutical Formulations Using Raman Spectroscopy Provides Insight into Polysorbate 20 Degradation Pathway. Pharm Res. 2015; 32(9): 2877-88.
39. Hall T, Sandefur S L, Frye C C, Tuley T L, Huang L. Polysorbates 20 and 80 degradation by group XV lysosomal phospholipase A2 isomer X1 in monoclonal antibody formulations. Journal of pharmaceutical sciences. 2016; 105(5):1633-42.

40. Brito R M, Vaz W L. Determination of the critical micelle concentration of surfactants using the fluorescent probe N-phenyl-1-naphthylamine. Analytical biochemistry. 1986; 152(2):250-5.
41. Hewitt D, Zhang T, Kao Y H. Quantitation of polysorbate 20 in protein solutions using mixed-mode chromatography and evaporative light scattering detection. J Chromatogr A. 2008; 1215(1-2):156-60.
42. Lapelosa M, Patapoff T W, Zarraga I E. Molecular simulations of micellar aggregation of polysorbate 20 ester fractions and their interaction with N-phenyl-1-naphthylamine dye. Biophys Chem. 2016; 213:17-24.
43. Nayem J, Zhang Z, Tomlinson A, Zarraga I E, Wagner N J, Liu Y. Micellar morphology of Polysorbate 20 and 80 and their ester fractions in solution via Small Angle Neutron Scattering. Journal of Pharmaceutical Sciences. 2019.

What is claimed is:

1. A polysorbate 20 composition comprising fatty acid esters comprising 1.0% or less caproate, greater than or equal to 2.6% and less than or equal to 6.6% caprylate, greater than or equal to 2.4% and less than or equal to 6.4% caprate, greater than or equal to 55.0% and less than or equal to 60.0% laurate, greater than or equal to 14.1% and less than or equal to 18.1% myristate, greater than or equal to 7.0% and less than or equal to 10.9% palmitate, and less than or equal to 2.0% stearate.

2. The composition of claim 1, comprising greater than or equal to 3%, or greater than or equal to 3.5%, or greater than or equal to 4%, or greater than or equal to 4.6%, and less than or equal to 6.6% of caprylate.

3. The composition of claim 1, comprising greater than or equal to 2.6%, or greater than or equal to 3%, or greater than or equal to 3.5%, or greater than or equal to 4%, or greater than or equal to 4.4%, and less than or equal to 6.4% caprate.

4. The composition of claim 1, comprising greater than or equal to 56%, or greater than or equal to 57%, or greater than or equal to 58%, and less than or equal to 60% laurate.

5. The composition of claim 1, comprising greater than or equal to 14.1% and less than or equal to 18%, or less than or equal to 17%, or less than or equal to 16%, or less than or equal to 15% myristate.

6. The composition of claim 1, comprising greater than or equal to 7% and less than 10.9%, or less than or equal to 10%, or less than or equal to 9%, or less than or equal to 8% palmitate.

7. The composition of claim 1, comprising less than or equal to 1.5%, or less than or equal to 1% stearate.

8. The composition of claim 1, comprising no detectable stearate.

9. The composition of claim 1, comprising 1% or less caproate, about 4.6% caprylate, about 4.8% caprate, about 57.0% laurate, about 16.2% myristate, about 9.4% palmitate, and no detectable stearate.

10. The composition of claim 1, comprising 1% or less caproate, from 3.7% to 5.2% caprylate, from 3.7% to 5.2% caprate, from 56.3% to 57.2% laurate, from 15.9% to 16.9% myristate, from 8.8% to 9.7% palmitate, and no detectable stearate.

11. The composition of claim 1, comprising 1% or less caproate, from 3.5% to 5.5% caprylate, from 3.5% to 5.5% caprate, from 55% to 58% laurate, from 15% to 17.5% myristate, from 8.5% to 10% palmitate, and about 0.1% stearate or less.

12. The composition of claim 1, further comprising greater than or equal to 5.8% and less than or equal to 9.8% oleate, and less than or equal to 2.0% linoleate.

13. A pharmaceutical formulation comprising a drug and a pharmaceutically acceptable excipient, wherein the pharmaceutically acceptable excipient comprises:
a polysorbate 20 composition comprising fatty acid esters, wherein the fatty acid esters of the polysorbate 20 composition comprise: 1.0% or less caproate, greater than or equal to 2.6% and less than or equal to 6.6% caprylate, greater than or equal to 2.4% and less than or equal to 6.4% caprate, greater than or equal to 55.0% and less than or equal to 60.0% laurate, greater than or equal to 14.1% and less than or equal to 18.1% myristate, greater than or equal to 7.0% and less than or equal to 10.9% palmitate, and less than or equal to 2.0% stearate.

14. The pharmaceutical formulation of claim 13, wherein the polysorbate 20 composition is from 0.01% to 0.12% (w/v) of the formulation.

15. The pharmaceutical formulation of claim 13, wherein the polysorbate 20 composition is from 0.01% to 0.08%, or from 0.03% to 0.1%, from 0.04% to 0.07%, (w/v) of the formulation.

16. The pharmaceutical formulation of claim 13, wherein the polysorbate 20 composition is about 0.01%, 0.02%, 0.03%, 0.04%, 0.05%, 0.06%, 0.07%, 0.08%, 0.09%, 0.10%, 0.11%, or 0.12% (w/v) of the formulation.

17. The pharmaceutical formulation of claim 13, wherein the fatty acid esters of the polysorbate 20 composition comprise greater than or equal to 3%, or greater than or equal to 3.5%, or greater than or equal to 4%, or greater than or equal to 4.6%, and less than or equal to 6.6% of caprylate.

18. The pharmaceutical formulation of claim 13, wherein the fatty acid esters of the polysorbate 20 composition comprise greater than or equal to 2.6%, or greater than or equal to 3%, or greater than or equal to 3.5%, or greater than or equal to 4%, or greater than or equal to 4.4%, and less than or equal to 6.4% caprate.

19. The pharmaceutical formulation of claim 13, wherein the fatty acid esters of the polysorbate 20 composition comprise greater than or equal to 56%, or greater than or equal to 57%, or greater than or equal to 58%, and less than or equal to 60% laurate.

20. The pharmaceutical formulation of claim 13, wherein the fatty acid esters of the polysorbate 20 composition comprise greater than or equal to 14.1% and less than or equal to 18%, or less than or equal to 17%, or less than or equal to 16%, or less than or equal to 15% myristate.

21. The pharmaceutical formulation of claim 13, wherein the fatty acid esters of the polysorbate 20 composition comprise greater than or equal to 7% and less than 10.9%, or less than or equal to 10%, or less than or equal to 9%, or less than or equal to 8% palmitate.

22. The pharmaceutical formulation of claim 13, wherein the fatty acid esters of the polysorbate 20 composition comprise less than or equal to 1.5% or less than or equal to 1% stearate.

23. The pharmaceutical formulation of claim 13, wherein the fatty acid esters of the polysorbate 20 composition comprise no detectable stearate.

24. The pharmaceutical formulation of claim 13, wherein the fatty acid esters of the polysorbate 20 composition comprise 1% or less caproate, about 4.6% caprylate, about 4.8% caprate, about 57.0% laurate, about 16.2% myristate, about 9.4% palmitate, and no detectable stearate.

25. The pharmaceutical formulation of claim 13, wherein the fatty acid esters of the polysorbate 20 composition comprise 1% or less caproate, from 3.7% to 5.2% caprylate, from 3.7% to 5.2% caprate, from 56.3% to 57.2% laurate, from 15.9% to 17.0% myristate, from 8.8% to 9.8% palmitate, and no detectable stearate.

26. The pharmaceutical formulation of claim 13, wherein the fatty acid esters of the polysorbate 20 composition comprise 1% or less caproate, from 3.5% to 5.5% caprylate, from 3.5% to 5.5% caprate, from 55% to 58% laurate, from 15% to 17.5% myristate, from 8.5% to 10% palmitate, and about 0.1% stearate or less.

27. The pharmaceutical formulation of claim 13, wherein the fatty acid esters of the polysorbate 20 composition further comprises, greater than or equal to 5.8% and less than or equal to 9.8% oleate, and less than or equal to 2.0% linoleate.

28. The formulation of claim 13, wherein the formulation has one or more of the following properties:
   a. the formulation comprises fewer free fatty acid particles resulting from degradation of fatty acid esters when compared to a formulation comprising a standard polysorbate 20 composition that is subjected to the same storage conditions;
   b. the number of free fatty acid particles produced by metal nucleation of free fatty acids in the formulation is less than the number of free fatty acid particles produced by metal nucleation of free fatty acids in a formulation comprising a standard polysorbate 20 composition that is otherwise identical in content and storage conditions; and
   c. degradation of fatty acid esters in the formulation results in free fatty acid particle formation that is delayed relative to free fatty acid particle formation in a composition or formulation comprising a standard polysorbate 20 composition.

29. The formulation of claim 13, further comprising a higher order ester degrading drug product, wherein up to 10% more fatty acid esters may be degraded to free fatty acids before free fatty acid particle formation is observed than in an HOE degrading drug product formulation comprising a standard polysorbate 20 composition that otherwise has the identical contents and is stored under the same conditions.

* * * * *